US009642390B2

(12) United States Patent
van Norren et al.

(10) Patent No.: US 9,642,390 B2
(45) Date of Patent: May 9, 2017

(54) NUTRITIONAL COMPOSITION FOR IMPROVING MUSCLE FUNCTION AND DAILY ACTIVITY

(75) Inventors: Klaske van Norren, Renkum (NL); Adrianus Lambertus Bertholdus van Helvoort, Wageningen (NL); Joyce Faber, Goor (NL); Robert Johan Joseph Hageman, Wageningen (NL); Arjan Paul Vos, Bennekom (NL)

(73) Assignee: N.V. Nutricia (NL)

( * ) Notice: Subject to any disclaimer, the term of this patent is extended or adjusted under 35 U.S.C. 154(b) by 0 days.

(21) Appl. No.: 12/980,727

(22) Filed: Dec. 29, 2010

(65) Prior Publication Data
US 2011/0152184 A1 Jun. 23, 2011

Related U.S. Application Data

(63) Continuation of application No. PCT/NL2009/050395, filed on Jul. 2, 2009, which is a continuation-in-part of application No. PCT/NL2008/050447, filed on Jul. 2, 2008.

(51) Int. Cl.
| | |
|---|---|
| *A61K 38/00* | (2006.01) |
| *A23L 33/19* | (2016.01) |
| *A23L 33/00* | (2016.01) |
| *A23L 33/12* | (2016.01) |
| *A23L 33/175* | (2016.01) |

(52) U.S. Cl.
CPC ............... *A23L 33/19* (2016.08); *A23L 33/12* (2016.08); *A23L 33/175* (2016.08); *A23L 33/40* (2016.08); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,080,788 | A * | 6/2000 | Sole et al. | 514/561 |
| 7,288,570 | B2 * | 10/2007 | Verlaan et al. | 514/561 |
| 8,372,425 | B2 * | 2/2013 | Loftsson et al. | 424/436 |
| 2003/0082287 | A1 | 5/2003 | Wolt et al. | 426/549 |
| 2006/0159746 | A1 * | 7/2006 | Troup et al. | 424/464 |
| 2007/0025980 | A1 * | 2/2007 | Krogsgaard et al. | 424/130.1 |
| 2013/0203658 | A1 * | 8/2013 | Luiking et al. | 514/4.8 |

FOREIGN PATENT DOCUMENTS

| | | |
|---|---|---|
| WO | 03/103415 A1 | 12/2003 |
| WO | 2004/026294 A1 | 4/2004 |
| WO | 2004/028434 A2 | 4/2004 |
| WO | 2004/056208 A1 | 7/2004 |
| WO | 2005/110124 A1 | 11/2005 |
| WO | 2007/043870 A1 | 4/2007 |
| WO | WO 2007043870 A1 * | 4/2007 |
| WO | 2007/069900 A1 | 6/2007 |

OTHER PUBLICATIONS

Bornet et. al., Dig Liver Dis. Sep. 2002; 34 Suppl. 2:S111-20.*
Lonnerdal, Am J Clin Nutr 2003;77(suppl):1537S-43S.*
ChemPep Inc. http://www.chempep.com/ChemPep-amino-acids.htm#Cysteine, 2014.*
http://ods.od.nih.gov/factsheets/Carnitine-HealthProfessional, May 10, 2013.*
Duarte, Comprehensive Reviews in Food Science and Food Safety vol. 9, 2010.*
International Preliminary Report on Patentability relating to corresponding PCT/NL2009/050395.
International Search Report relating to corresponding PCT/NL2009/050395.
Office Action issued for corresponding European Patent Application No. 09773790.2, dated Mar. 15, 2012.
Abbott GmbH & Co. KG: Medizinische Ernahrung—Produkte—Spezialdiaten• ProSure. http://www .abbott.de/MedizinischeErnaehrung/ Produkte/ Spezialdiaten/ ProSure/ prosure. htm—published: Dec. 8, 2003.
Abbott: ProSure™ gibt Kraft fur das Leben. Facsimile received by Fresenius Hamburg on Nov. 1, 2002.
Abstracts submitted by the patentee during examination of the opposed patent—uploaded: Sep. 25, 2012.
Barber et al.: Effect of a Fish Oil-Enriched Nutritional Supplement on Metabolic Mediators in Patients With Pancreatic Cancer Cachexia. Nutrition and Cancer, 4 {2), 118-124—published: 2001.
Colker et al., Effects of Supplemental Protein on Body Composition and Muscular Strength in Healthy Athletic Male Adults, Current Therapeutic Research, 61, Jan. 2000.
CrossFit Discussion Board: Skim milk vs. whole milk. http://board.crossfit.com/showthread.php?t=36978—downloaded: Jun. 12, 2014—published: Sep. 13, 2008.
da Silva : Nutritional Patient Monitoring—Malignant neoplasm Breast with Liver Metastasis (in Portuguese) . Sao Judas Tadeu University , School of Biological and Health Sciences—published: 2007.

(Continued)

*Primary Examiner* — Jeanette Lieb
(74) *Attorney, Agent, or Firm* — Banner & Witcoff, Ltd.

(57) ABSTRACT

The invention relates to a nutritional composition comprising
(a) at least 18 en % of proteinaceous matter, said proteinaceous matter comprising whey;
(b) at least 12 wt % of leucine, based on total proteinaceous matter; and
(c) a lipid fraction comprising at least a ω-3 polyunsaturated fatty acid selected from the group of eicosapentaenoic acid, docosahexaenoic acid, eicosatetraenoic acid and docosapentaenoic acid for improving the muscle function in a mammal, for improving daily activity, for improving physical performance, for providing a better prognosis in terms of extended life-expectancy, for improving compliance to an anti-cancer therapy or for improving a quality of life.

26 Claims, 10 Drawing Sheets

(56) References Cited

OTHER PUBLICATIONS

Daly: Independent and Combined Effects of Exercise and Vitamin D on Muscle Morphology, Function and Falls in the Elderly. Nutrients 2, 1005-1017—published: 2010.
Faber et al.: Beneficial immune modulatory effects of a specific nutritional combination in a murine model for cancer cachexia. British Journal of Cancer 99, 2029-2036—published: Nov. 18, 2008.
Glycemic Index for Sweeteners. http:/ /www.sugar-and-sweetener-guide.com/glycemic- index-for-sweeteners. html—downloaded: Jul. 16, 2014.
Gomad: How to gain 25 lbs in 25 days with squats & milk. http://stronglifts.com/gomad-milk-squats-gallon-gain-weight/—downloaded: Jun. 12, 2014—published: Jun. 15, 2009.
Gorselink et al.: Mass-dependent decline of skeletal muscle function in cancer cachexia. Muscle Nerve 33(5):691-3—published: May 2006.
Hebeisen et al.: Increased Concentrations of Omega-3 Fatty Acids in Milk and Platelet Rich Plasma of Grass-Fed Cows. Internal. J. Vit. Nutr. Res. 63, 229-233—published: 1993.
Insulin Resistance Accelerates Muscle Protein Degradation: Activation of the Ubiquitin-Proteasome Pathway by Defects in Muscle Cell Signaling, Endocrinology, 147(9): 4160-4168, 2006.
Journees d'etudes de l'ADLF: Symposium Prosure—Aliment dietetique destine a des fins m edicales speciales. Abbott Nutrition—published: March.
Kessler: Lebensmittel—und Bioverfahrenstechnik—Molkereitechnologie. Verlag A. Kessler, Munchen 1996.
Le role de EPA pharmaco-nutriment actif sur l'amaigrissement associe a la maladie cancerieuse. Abbott France—published: 2001.
Lorite et al., Induction of muscle protein degradation by a tumour factor, British Journal of Cancer, 76(8): 1035-1040, 1997.
Ludwig : The Glycemic Index—Physiological mechanisms relating to obesity , diabetes and cardiovascular disease. JAMA, May 8, 2002—vol. 287, No. 18—published: 2002.
Machine Translation of da Silva : Nutritional Patient Monitoring—Malignant neoplasm Breast with Liver Metastasis (in Portuguese) . Sao Judas Tadeu University , School of Biological and Health Sciences—published: 2007.
Machine Translation of Nutricia Medical Oy: Nutricia—Forticare (in Finnish). Published : Apr. 2009.
Machine Translation of van der Meij et al.: Relevance of diet enriched with fish oil (Epa) in cancer (in Dutch) . Report released by the National Working Dietitians Oncology (Lwdo) commissioned by Kwf- published: Mar. 2005.
Neu von Pfrimmer Nutricia: FortiCare™ gegen tumorbedingte Mangelernahrung.http:/ / www .nut ricia.de/ aktuelles/ news_archiv/ neu_von_pfrim mer_nutricia_f orticare_gegen_tumorbedingte_mangelernaehrung/—downloaded: May 28, 2014—published: Sep. 10, 2004.
Nutricia Medical Oy: Nutricia—Forticare (in Finnish). Published : Apr. 2009.
Nutrition medicale Abbott—Complementation orale . Abbott Nutrition• published: 2001.
O'Keefe et al., Dietary Strategies for Improving Post-Prandial Glucose, Lipids, Inflammation, and Cardiovascular Health, Journal of the American College of Cardiology, 51 (3), 2008.
Office Action issued for corresponding European Patent Application No. 2317878, dated Aug. 6, 2014.
Office Action issued for corresponding European Patent Application No. 2317878, dated Jul. 31, 2014.
Product handbook Prosure—http ://ross.com—published: Dec. 11, 2003.
ProSure—Start as early as possible. Abbott Laboratories—published: May 2002.
Rieu et al., Leucine supplementation improves muscle protein synthesis in elderly men and independently of hyperaminoacidaemia, J Physiol, 575.1: 305-315, 2006.
Ross Prosure—http://www .prosure.com/—published: Dec. 8, 2003.
Roy: Milk: the new sports drink? A Review. Journal of the International Society of Sports Nutrition 5:15—published: Oct. 2, 2008.
Ryan et al.: Enteral Nutrition Enriched With Eicosapentaenoic Acid (EPA) Preserves Lean Body Mass Following Esophageal Cancer Surgery: Results of a Double-Blinded Randomized Controlled Trial. Annals of Surgery 249(3), 355-363—published : Mar. 2009.
Santschi et al.: Colostrum and milk fatty acids of dairy cows as influenced by extruded linseed supplementation during the transition period. Can. J. Anim. Sci. 89: 383-392—published: 2009.
Siddiqui et al., Nutrition Modulation of Cachexia/Proteolysis, Nutrition in Clinical Practice, 21: 155-167, Apr. 2006.
Smith et al., Effect of eicosapentaenoic acid, protein and amino acids on protein synthesis and degradation in skeletal muscle of cachectic mice, British Journal of Cancer, 91: 408-412, 2004.
The University of Sydney: GI Database—ProsureTM , ready-to-drink supplement, vanilla flavor (Abbott Nutrition International). http://glycemicindex.com/foodSearch.php?num= 1616&ak= detail• downloaded: May 21, 2014.
The University of Sydney: GI Database—Whole milk. http:// glycemicindex.com/foodSearch.php—downloaded: Jun. 12, 2014.
Thompson: The Glycemic Load Diet. McGraw-Hill, 2006.
van der Meij et al.: Relevance of diet enriched with fish oil (EPA) in cancer (in Dutch) . Report released by the National Working Dietitians Oncology (LWDO) commissioned by KWF—published: Mar. 2005.
van Norren et al.: A specific nutritional composition for cancer patients with a low glycemic index. Clinical Nutrition Supplements 4(2), p. 77—published: Sep. 2009.
van Norren et al.: Dietary supplementation with a specific combination of high protein, leucine, and fish oil improves muscle function and daily activity in tumour-bearing cachectic mice. British Journal of Cancer 100, 713-722—published: Mar. 3, 2009.
Ward, Whey proteins, 2008.
Web Archive: www.forticare .de.https://web. arch ive.org/web/ 20080 101 085006/ http://www .fort icare. del—downloaded: Jun. 3, 2014—published: Jan. 1, 2008.
Whey (sweet), in: Souci, Fachmann, Kraut: Food composition and nutrition tables, CRC Press, Taylor and Francis Group, Boca Raton—published: 2008.
Communication re corresponding European Patent No. 2317878 dated Apr. 6, 2016.
Communication re corresponding European Patent No. 2317878 dated Jun. 3, 2016.
Communication re corresponding European Patent No. 2317878 dated Apr. 13, 2016.
Communication re corresponding European Patent No. 2317878 dated Apr. 5, 2016.
Skimmed Milk, https://en.wikipedia.org/wiki/skimmed_milk, downloaded Mar. 12, 2015.
Van Der Meij, B.S., et al, Oral nutritional supplements containing n-3 polyunsaturated fatty acids affect quality of life and functional status in lung cancer patients during multimodality treatment: an RCT, European Journal of Clinical Nutrition, Jan. 11, 2012, pp. 399-404, No. 66.
Moses, A.G., et al, An experimental nutrition supplement enriched with n-3 fatty acids and antioxidants is associated with an increased physical activity level in patients with pancreatic cancer cachexia, Clinical Nutrition—Supplements Only, Aug. 2001, p. 21, supp. 3, vol. 20.
Fearon, K. C. H., et al, Effect of a protein and energy dense n-3 fatty acid enriched oral supplement on loss of weighl and lean tissue in cancer cachexia: a randomised double blind trial, Gut, Mar. 18, 2003, pp. 1479-1486, vol. 52.
Kennis, Eva, et al, Longitudinal impact of aging on muscle quality in middle-aged men, Age, Aug. 8, 2014, pp. 1-12, vol. 36, No. 9689.
Heatwole, Chad R., et al, An Open-Label Trial of Recombinant Human Insulin-Like Growth Factor-I/Recombinant Human Insulin-Like Growth Factor Binding Protein-3 (rhIGF-1/rhIGFBP-3) in Myotonic Dystrophy Type 1, National Institute of Health, PA Author Manuscript, Jan. 2011, pp. 1-20.

(56) References Cited

OTHER PUBLICATIONS

Anker, Stefan D., et al, Evidence for partial pharmaceutical reversal of the cancer anorexia-cachexia syndrome: the case of anamorelin, Journal of Cachexia, Sarcopenia and Muscle, Aug. 30, 2015, pp. 275-277, vol. 6.

Hayes, Alan, et al, Effect of whey protein isolate on strength, body composition and muscle hypertrohy during resistance training, Current Opinion in Clinical Nutrition and Metabolic Care, 2008, pp. 40-44, vol. 11.

Salmen, Saleh H., et al, Amino acids content and electrophoretic profile of camel milk casein from different camel breeds in Saudi Arabia, Saudi Journal of Biological Sciences, 2012, pp. 177-183, vol. 19.

Abbott: Prosure™ Everything to Gain article, web archive, downloaded Mar. 17, 2016.

Food energy—methods of analysis and conversion factors, Food and Agriculture Organization of the United Nations, FAO Food and Nutrition Paper, Report of a technical workshop, Rome, Dec. 3-6, 2002, No. 77, ISSN 0254-4725, 2003.

Zhixiong, Liu,"Typical Orthopaedic Diagnostic Classification Methods and Functional Evaluation Standards."

English Translation of Zhixiong, Liu,"Typical Orthopaedic Diagnostic Classification Methods and Functional Evaluation Standards."

European Search Report issued from corresponding EP Application No. 13191671.0, dated Dec. 17, 2013.

Feng, Hai, "Yundong Xuancai Xue", p. 116, Chengdu, Sichuan People's Publishing House, Sep. 2008, the 1st edition, Sep. 30, 2008.

Third Party Observation issued for corresponding European Patent Application No. 2695528, dated Oct. 27, 2016.

English Translation of Office Action issued for corresponding Japanese Patent Application No. 2014102469930, dated Nov. 2, 2016.

* cited by examiner

NUTRITIONAL COMPOSITION FOR IMPROVING MUSCLE FUNCTION AND DAILY ACTIVITY

RELATED APPLICATIONS

This application is a continuation of PCT application number PCT/NL2009/050395 designating the United States and filed Jul. 2, 2009; which claims the benefit of PCT application number PCT/NL2008/050447 and filed Jul. 2, 2008 both of which are hereby incorporated by reference in their entireties.

DESCRIPTION

The invention relates to a composition comprising proteinaceous matter that comprises leucine and an ω-3 polyunsaturated fatty acid.

The invention also relates to the use of a composition suitable for improving the muscle function of a mammal. The invention also relates to the use of a composition suitable for improving daily activity of a mammal.

BACKGROUND

Body composition, muscle functionality and daily activity are clinically highly relevant parameters, because muscle function and daily activity are important contributors to the quality of life of a cancer patient. Furthermore, an improved physical condition of a patient, as reflected in body composition and physical performance, might contribute to its compliance to an anti-cancer therapy. E.g. the dose of chemotherapy can be provided as scheduled, instead of being adjusted to a lower body weight of the patient.

Cachexia is one of the most debilitating aspects of cancer and has been associated with increased morbidity and mortality, with a reduced quality of life, an impaired response to chemotherapy, an increased susceptibility to chemotherapy-induced toxicity and higher incidence of post-operative complications. Cancer cachexia can be defined as involuntary weight loss with a depletion of not only fat mass but also lean body mass due to muscle wasting. Symptoms besides mass loss are debilitation, weakness, edema, an impaired immune response and decline of motor and mental function. Cachectic patients have been shown to have higher resting energy expenditure which is not met by an increased nutrient intake, in many cases food intake is even reduced. Hence, approximately 45% of cancer patients loose more than 10% of their pre-diagnostic mass. The tumor can induce metabolic changes in protein metabolism, resembling those found in infection or injury. These changes are characterized by net protein breakdown and increased oxidation of branched-chain amino acids (BCAAs) in muscle to support energy supply and synthesis of gluconeogenic amino acids. The breakdown of host protein is partly stimulated by inflammatory mediators produced by the host (e.g. TNFα, IL-6)(1), but also by the tumor, through the release of a proteolysis inducing factor (PIF)(4). Moreover, the tumor has a high intrinsic protein synthesis rate and has the capacity for intracellular transport and catabolism of BCAAs.

An increased energy demand and an inflammatory catabolic status leads to an important reduction in body fat content and more worse muscle mass. It is therefore, hypothesized that nutritional support in cancer patients should aim more for counteracting net body protein breakdown, than for merely increasing caloric intake per se. In order to establish a new, positive balance in protein synthesis and breakdown, supplementation of protein should be combined with components modifying and mitigating the catabolic signal. A high amino acid supply has been described to be essential for increasing protein synthesis. BCAAs and especially leucine are known to control skeletal muscle protein metabolism by stimulating protein synthesis and inhibiting protein breakdown. Prospective caloric- and nitrogenous-controlled trials of BCAA supplementation via TPN in septic patients indeed resulted in an improvement of pre-albumin levels and decreased overall mortality in a patient group with a high Simplified Acute Physiology Score (LeGall-SAPS) classification. Supplementation of tumor-bearing rats with a diet supplemented with 3% leucine has been reported to reduce loss of lean body mass, gastrocnemius muscle mass and myosin content, when compared to an isonitrogenous and isocaloric control diet. These data are supported by the observation that leucine increased protein synthesis in pregnant tumor-bearing rats, possibly resulting from changes in the ubiquitin-proteasome system. Two clinical trials studied oral BCAA supplementation after surgical removal of the tumor and reported a shorter hospital stay, a better performance status at 3 months and an increased body mass at 1 year. BCAAs have also been supplemented in the presence of the tumor: patients undergoing chemotherapy received oral BCAA supplementation up to 1 year, resulting in a lower overall morbidity, improved nutritional status and better quality of life. Other nutrients which may have anti-cachectic effects are ω-3 polyunsaturated fatty acids (PUFAs). The vast majority of the clinical trials in which ω-3 PUFAs were tested report an increase or maintenance of body mass (BW); while in two clinical trials no effect on the loss of BW was found. In the latter, however, the supplementation period was only 2 weeks and/or included only a small number of patients. Other effects of EPA or fish oil supplementation in cancer patients, were a net lean tissue gain, an increase in total resting energy expenditure and physical activity level, a decrease in need for TPN and an improved quality of life, and even suggested improved survival.

WO 2004/026294 discloses nutritional compositions comprising a mixture of essential amino acids in free form and/or in salt form, rather than intact protein, for the promotion of muscle protein synthesis or controlling tumor-induced weight loss, such as cancer cachexia. Intact protein may be present in addition. However, a nutritional composition comprising at least 18 en % proteinaceous matter, at least part of which is whey protein, at least 12 wt. % leucine and an ω-3 polyunsaturated fatty acid selected from the group of eicosapentaenoic acid, docosahexaenoic acid, eicosatetraenoic acid and docosapentaenoic acid is not described in a single combination. Exemplified nutritional compositions comprise caseinate as protein source. In Example 2 of WO 2004/026294, it is concluded that ingestion of free essential amino acids is more effective than ingestion of a comparable amount of intact protein in stimulating net muscle protein synthesis.

EP 1 774 973 A1 discloses a composition comprising proteinaceous matter, said proteinaceous matter providing at least 24 en % and at least 12 wt % of leucine, based on total proteinaceous matter, for the treatment of insulin resistance. No compositions were exemplified.

DESCRIPTION OF THE INVENTION

Figure 1A:
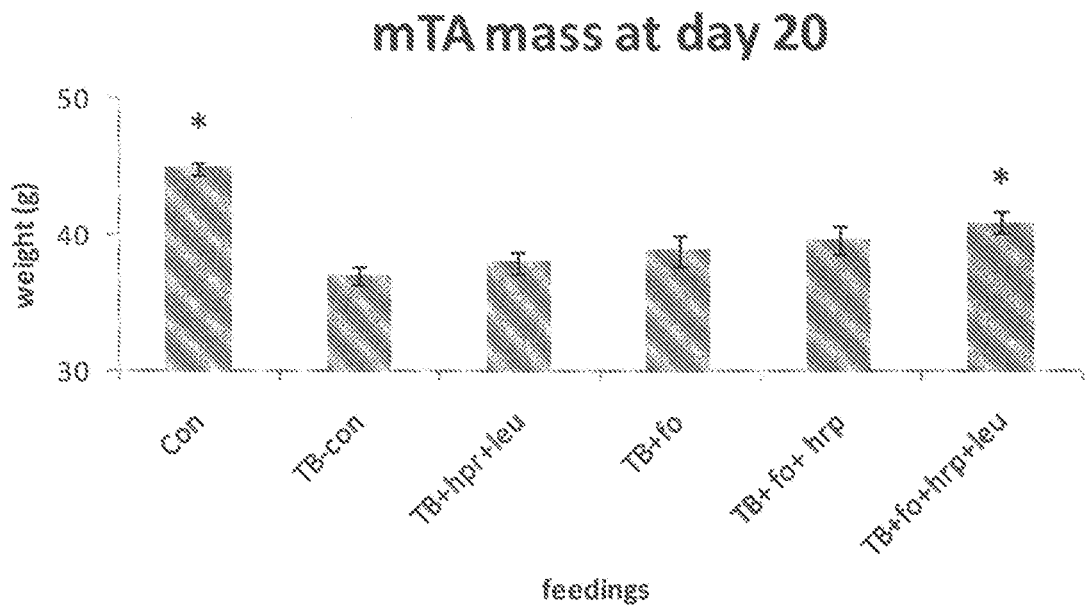
FIGS. 1A and 1B depict the differences in muscle Tibialis Anterior mass (FIG. 1A) and Epididymal fat mass after different interventions (FIG. 1B).

It is an object of the invention to provide a composition suitable for improving the muscle function, preferably leading to an improvement in daily activities of a mammal. In particular, it is an object of the present invention to provide a nutritional composition for such purpose.

It has now been found that it is possible to treat a subject with a reduced muscle function or being at risk of developing a reduced muscle function with a specific composition comprising proteinaceous matter.

Accordingly, the present invention relates to a combination of whey protein, leucine and at least one at least a ω-3 polyunsaturated fatty acid selected from the group of eicosapentaenoic acid, docosahexaenoic acid, eicosatetraenoic acid and docosapentaenoic acid for improving the muscle function in a mammal.

The invention further relates to the a combination of whey protein, leucine and at least one at least a ω-3 polyunsaturated fatty acid selected from the group of eicosapentaenoic acid, docosahexaenoic acid, eicosatetraenoic acid and docosapentaenoic acid for a use selected from the group of improving daily activity, improving physical performance, providing a better prognosis in terms of extended life-expectancy, improving compliance to an anti-cancer therapy and improving a quality of life. This use may be in addition to improving the muscle function in a mammal or independent thereof.

Such a combination may in particular be in the form of a specific nutritional composition.

Accordingly, the present invention in particular relates to a nutritional composition, comprising
(a) at least 18 en % of proteinaceous matter, said proteinaceous matter comprising whey;
(b) at least 12 wt % of leucine, based on total proteinaceous matter; and
(c) a lipid fraction comprising at least a ω-3 polyunsaturated fatty acid selected from the group of eicosapentaenoic acid, docosahexaenoic acid, eicosatetraenoic acid and docosapentaenoic acid.

In particular such composition may be used for improving the muscle function in a mammal.

Alternatively or in addition, the composition may in particular be used for a use selected from the group of improving daily activity, improving physical performance, providing a better prognosis in terms of extended life-expectancy, improving compliance to an anti-cancer therapy and improving a quality of life.

When referring to a composition comprising whey protein (or in short: whey), leucine and at least one of said ω-3 polyunsaturated fatty acids for a specific purpose—such as for improving the muscle function in a mammal—it is in particular meant these said components are intended to be used for that purpose in combination. Accordingly, each of said components is considered to play a role in accomplishing that purpose.

The energetic value of a compound (en %) is based on the energy provided by the digestible part (in particular in a human) of the compound. In particular, the energetic value is based on the contribution of proteinaceous matter, lipids and digestible carbohydrates, using the following calculation factors: 4 kcal/g for digestible carbohydrates and proteinaceous matter and 9 kcal/g for lipids.

Preferably, the organoleptic properties of the composition are such that the consumption is generally appreciated as pleasant.

Preferably, the composition passes the stomach easily.

Preferably, the digestible components of the composition become readily available upon intake of the product.

A composition according to the invention may in particular be used to improve skeletal muscle function in a mammal. It is understood that improving skeletal muscle function may comprise improving either one or both of muscle mass dependent and muscle mass independent loss of muscle function in a mammal. For muscle mass dependent muscle function loss, it may comprise a correction in maximal force, maximal contraction velocity or maximal relaxation velocity of skeletal muscle. For muscle mass independent loss of muscle function, it may comprise a correction in maximal force corrected for muscle mass, maximal contraction velocity corrected for muscle mass or maximal relaxation velocity corrected for muscle mass. Furthermore, the time needed for a contraction or relaxation might be improved.

In an embodiment, a composition of the invention may be used to prevent or treat a reduction of muscle function due to, or resulting from aging, disease, disorder, drugs or trauma, preferably drug, disease or disorder.

Reduced muscle function may in particular manifest itself as a symptom due to a disease or disorder such as cancer, HIV infection, COPD, renal failure, heart failure, and a disease state characterized by a high plasma and/or serum level of pro-inflammatory cytokines Hence, the composition of the invention may in particular be used for treating a mammal suffering from a disease or disorder selected from the group of cancer, HIV infection, COPD, renal failure, heart failure, and a disease state characterized by a high plasma and/or serum level of pro-inflammatory cytokines.

Preferably, the disease or disorder is a cancer. In this context the reduced muscle function may be a muscle mass dependent function loss or a muscle mass independent function loss.

Moreover, treatment with drugs such as chemotherapy might lead to decrease in muscle function. Therefore, the invention relates also to a nutritional composition according to the invention, wherein the drug is administered in the framework of a chemotherapy.

Based on experiments wherein compositions according to the invention are fed to tumour-bearing mice, as illustrated in the example below, it is contemplated by the inventors that a composition of the invention is effective in improving the muscle function of a mammal. It was shown in the experiments that at least one of several physiological parameters associated with a reduced muscle function was positively affected.

It is further contemplated that a composition of the invention may be used to provide a better prognosis in terms of extended life-expectancy and/or a better quality of life. Factors improving the quality of life are in particular less fatigue, improved daily activity, more stamina, improved contrast between day time and night time activity (nocturnal sleep), better general condition and less periods of feeling depressed.

Proteinaceous Matter

Proteinaceous matter is formed by moieties formed from amino acids. The term amino acids as used herein includes amino-acid residues (e.g. in peptides). In particular, the term 'proteinaceous matter' includes free amino acids, amino acid salts, amino acid esters, the amino acid residues bound to conjugating molecules and peptides, including proteins. Likewise, when reference is made to a specific amino acid, e.g. leucine, this is meant to include the specific amino acid (residues) present as a salt, in a bound form, as well as the free specific amino acid.

With a peptide is meant a combination of two or more amino acids, connected via one or more peptidic bonds. When incorporated in a peptide, amino acids are named amino-acid residues. Peptides include oligopeptides and polypeptides, including proteins.

With a polypeptide is meant a peptide chain comprising 14 or more amino-acid residues. With an oligopeptide is meant a peptide chain comprising 2 to 13 amino-acid residues.

Chiral amino acids present in a composition of the invention may be in the L-form or the D-form. Usually, the chiral amino acids present in a composition of the invention are in the L-form.

In an embodiment, a liquid composition according to the invention comprises at least 7 g/100 ml of proteinaceous matter, preferably at least 8 g/100 ml, more preferably at least 9 g/100 ml, most preferably at least 10 g/100 ml.

The proteinaceous matter in a composition of the invention provides at least 18 en %, preferably at least 20 en %, more preferably at least 22 en % of the total composition. The proteinaceous matter in a composition of the invention usually provides 60 en % or less, preferably 40 en % or less, or more preferably 32 en % or less of the total composition.

The proteinaceous matter comprises whey protein. Whey protein is in inter alia considered advantageous, because it has a fast post-prandial release of amino acids into blood, compared to e.g. casein. Thus, the inventors realised the threshold concentration of amino acids needed to switch on the anabolic signal of muscle protein synthesis can be reached easier (e.g. at a lower dosage of proteinaceous matter, or sooner after ingestion).

The proteinaceous matter may further comprises proteinaceous matter from one or more other protein sources, in particular one or more proteinaceous matter sources selected from the group of casein, caseinate, soy and wheat, preferably casein. Said protein source or part thereof may have been modified, in particular by (partial) hydrolysis.

With whey is meant a source of a globular protein that can be isolated from whey. In particular, globular whey proteins can be selected from beta-lactoglobulin, alpha-lactalbumin and serum albumin, including mixtures thereof. Examples of mixtures that contain whey proteins are whey isolate and whey concentrate. Both sources contain predominantly intact whey proteins, which is preferred in the context of this application.

In an embodiment, the proteinaceous matter comprises at least 10 wt %, preferably at least 15 wt %, more preferably at least 20 wt %, most preferably at least 25 wt % of whey, based on the total proteinaceous matter. Usually, the whey fraction is 50 wt. % or less based on total proteinaceous matter, in particular 40 wt % or less based on total proteinaceous matter, although—if desired—more than 50 wt. % to 100% of the proteinaceous matter may be provided by whey.

In particular, in case of a liquid composition, the concentration of denatured whey preferably does not exceed 35 wt % based on total proteinaceous matter. This is advantageous with respect to avoiding the risk of gelation during storage. Also, the choice of whey over free amino acids is preferred as free amino acids have a bad taste.

The presence of whey may offer a number of advantages. The whey shows an advantageous release behaviour both in terms of release rate of the amino acids and the tendency to make the amino acids available for uptake by the body, essentially at the same time.

The advantageous amino-acid release behaviour may be further enhanced by (slightly) hydrolysing at least part of the whey protein, usually to the extent that up to 20% of the protein is hydrolysed to free amino acids, preferably to the extent that up to 10% of the protein is hydrolysed to free amino acids.

For said enhanced effect usually 50 wt % of the whey protein or less is (slightly) hydrolysed, in particular 10 to 50 wt %.

If desired the free amino acid or part thereof may be removed from the hydrolysate. Suitable techniques are known, e.g. filtration, chromatography or absorption.

As the source for whey protein(s) preferably a whey fraction is chosen comprising less that 20 wt % casein glycomacropeptide (GMP), more preferably less than 10 wt %.

The beta-lactoglobulin content preferably is larger than 40 wt %, more preferably 46 to 80 wt %.

When used as intact protein, the casein preferably comprises a high concentration of beta casein, in particular more than 36 g/100 g casein, more in particular 38 to 70 g/100 g casein.

In an embodiment, at least part of the proteinaceous matter is present in the form of free amino acids, a salt thereof or as a conjugate with a conjugating molecule other than a protein or peptide, which conjugate is capable of being split in the free amino acid (or salt thereof) and the conjugating compound under the influence of a bile constituent and/or a pancreas excretes in duodenum and/or the ileum. In an embodiment, the amount of amino acid in such form, in particular in the form of a salt or the free form, is up to 15 wt % based on total proteinaceous matter, preferably 0.5-14 wt %.

The peptide content (oligopeptide, polypeptide, protein) based on total proteinaceous matter is usually at least 50 wt %, at least 60 wt % or at least 75 wt %. The wt % of peptide based on total proteinaceous matter is usually up to 99 wt %, preferably up to 94 wt %, more preferably 89 wt %.

An advantage of a composition wherein the peptide content is high (≥50 wt %) is that the taste, or another organoleptic property of the composition, usually is appreciated better when consumed (orally). Further, the uptake of amino acids by the body may be more gradual.

In a particular embodiment, the composition comprises leucine in the form of a free acid, a salt, a dipeptide or a conjugate with a conjugating compound other than an amino acid, a protein, or a peptide, which conjugate is capable of being split into the free amino acid (or salt thereof), preferably in the gut or stomach or after absorption in the enterocytes or liver.

Leucine is preferably for at least 35 wt %, more preferably for at least 40 wt %, based on the total proteinaceous leucine, present in the form of a peptide (oligopeptide, polypeptide, protein), preferably in the form of polypeptides and/or (intact) proteins.

Leucine is for up to 100 wt %, preferably for up to 80 wt %, based on the total proteinaceous leucine, present in the form of a peptide (oligopeptide, polypeptide, protein), more preferably in the form of one or more polypeptides and/or one or more (intact) proteins.

The leucine content in a composition of the invention is at least 12 wt %, at least 13 wt %, at least 16 wt % or at least 19 wt %, based on total proteinaceous matter. Usually the leucine content is 50 wt % or less, In particular, it may be 30 wt % or less, 25 wt % or less or 23 wt % or less, based on total proteinaceous matter. In an embodiment, the leucine content is 12 to 23 wt %, based on total proteinaceous matter.

Advantageously, the composition may comprise glutamine and/or glutamic acid.

If present, the glutamine content (determined as total glutamine & glutamic acid) is at least 15 wt %, based on total proteinaceous matter. In an embodiment, the glutamine content is 16 to 28 wt %, preferably 17 to 26 wt %, based on total proteinaceous matter.

Advantageously, the composition may comprise one or more of the group of cystine, cysteine and cysteine equivalents such as N-acetyl cysteine. preferably in an amount of at least 0.8 wt %, based on total proteinaceous matter. Usually the content of cystine, cysteine and cysteine equivalents is 11 wt % or less, In particular, it is 8 wt % or less, based on total proteinaceous matter. In an embodiment, the content of cystine, cysteine and cysteine equivalents is 0.8 to 8 wt %, based on total proteinaceous matter.

Glutathione homeostasis plays a role in maintaining whole body resistance to oxidative stress. Severe oxidative stress in the muscle might lead to decreased muscle function. In experiments with tumour-bearing mice, the inventors found that glutathione levels of the liver were significantly decreased. The liver is the main distributor of glutathione and therefore liver glutathione is a good reflection of whole body glutathione. Surprisingly, further experiments by the inventors revealed that at least partial normalization of the glutathione level in liver cells occurred under the influence of glutamine and/or cysteine in a composition of the invention. Particularly good results were obtained when both amino acids were present in the composition. Based on these experiments, it is contemplated by the inventors that a composition of the invention comprising glutamine or cysteine, preferably in a concentration as indicated above, is particularly effective in improving the muscle function of a mammal. It is further contemplated that the presence of both glutamine and cysteine in a composition of the invention is even more effective in improving the muscle function of a mammal.

In an embodiment, an advantageous effect of glutamine and/or cysteine on the muscle function of a mammal is obtained with a composition of the invention comprising whey protein and casein.

In a composition according to the invention the weight ratio leucine/(valine+isoleucine) is generally 1.0 or more, preferably 1.05 or more.

In the total product the content of essential amino acids usually is at least 49 wt %, preferably 49 to 80 wt %, more preferably 52 to 70 wt % of the total proteinaceous matter is formed by essential amino acids.

The lysine content usually is 7 to 15 g/100 g of proteinaceous matter, preferably 7.5 to 14 g/100 g of proteinaceous matter.

Decreasing muscle protein breakdown with the composition of the invention may also help reduce carnitine and/or lysine loss from catabolic muscle and help maintain muscle carnitine and lysine levels. In this way, the composition of the invention comprising carnitine might aid to skeletal muscle function. L-carnitine (beta-acetoxy-gamma-N, N, N-trimethylaminobutyrate) is synthesized from the essential aminoacids lysine and methionine mainly in liver and kidney. Carnitine is required for the transport of medium/long-chain fatty acids across mitochondrial membranes, which then can enter beta-oxidation. In addition, it facilitates the removal of short chain organic acids from mitochondria, thereby freeing intramitochondrial coenzyme-A to participate in the beta-oxidation and Krebscycle. Because of these key functions, carnitine is concentrated in tissues that use fatty acids as a primary dietary fuel, such as skeletal and heart muscle.

Carnitine deficiency has been reported in several forms of cancer and has been associated with increased fatigue. Three open labels studies indeed suggest that treatment with carnitine reduced fatigue, measured with a fatigue score. Especially one derivative of carnitine, acid-soluble acyl-carnitine seems to be decreased in cancer patients compared to healthy controls. For total carnitine, a significant decrease has been reported after three months of therapy and seems to suggest that carnitine deficiency is induced by chemotherapy. Another explanation for the onset of a carnitine deficiency may be that the decrease in carnitine levels is associated with the presence of cachexia. In conclusion, carnitine deficiency seems to be induced by both chemotherapy and progression of disease (cachexia). These findings suggest that supplementation with a composition of the invention comprising carnitine may best start immediately after diagnosis in order to prevent a deficiency.

If present, the carnitine content in a composition of the invention is usually at least 5 mg per 100 kcal, preferably at least 10 mg per 100 kcal, at least 25 mg per 100 kcal or at least 100 mg per 100 kcal. Usually the carnitine content is 2.5 g or less per 100 kcal, in particular 1.25 g or less per 100 kcal. In case of a liquid product, the carnitine content is preferably at least 10 mg/100 ml, at least 50 mg/100 ml or at least 200 mg/100 ml. Usually the carnitine content is 5 g or less per 100 ml, in particular 2.5 g or less per 100 ml.

Taurine is the most abundant free amino acid in cardiac and skeletal muscle and with decrease of muscle mass it is excreted from the muscle. Taurine is thought to play an important role in ion movement and calcium handling of the muscle and might therefore influence muscle performance. Taurine depletion causes cardiomyocyte atrophy, mitochondrial and myofiber damage and cardiac dysfunction, effects likely related to the actions of taurine. Decreasing muscle protein breakdown using a composition of the invention may also help reduce taurine loss from catabolic muscle and help maintain muscle taurine levels and in this way maintain muscle function.

If present, the taurine content in a composition of the invention is usually at least 5 mg per 100 kcal, preferably at least 10 mg per 100 kcal, at least 25 mg per 100 kcal or at least 100 mg per 100 kcal. Usually the taurine content is 2.5 g or less per 100 kcal, in particular 1.25 g or less per 100 kcal. In case of a liquid product, the taurine content is preferably at least 10 mg/100 ml, at least 50 mg/100 ml or at least 200 mg/100 ml. Usually the taurine content is 5 g or less per 100 ml, in particular 2.5 g or less per 100 ml.

Lipid Fraction

In a composition of the invention, the lipid fraction usually provides at least 10 en %, preferably at least 20 en % or more preferably at least 25 en % of the total composition. The lipid fraction in a composition of the invention usually provides 50 en % or less, preferably 40 en % or less, or more preferably 35 en % or less of the total composition.

With the term 'lipid fraction' is meant a fraction comprising one or more lipids, including fatty acids, fatty-acid derivatives (including tri-, di-, and monoglycerides and phospholipids) and sterol-containing metabolites such as cholesterol.

As indicated above, a composition of the invention comprises at least one ω-3 polyunsaturated fatty acid selected from the group of eicosapentaenoic acid (EPA), docosahexaenoic acid (DHA), eicosatetraenoic acid (ETA) and docosapentaenoic acid (DPA).

A composition of the invention may further comprise ω-3 and/or ω-6 polyunsaturated fatty acids, in particular those containing 18 to 26 carbon atoms, e.g. linolenic acid (LA), alpha linolenic acid (ALA), gamma linolenic acid (GLA), dihomo gamma-linolenic acid (DGLA) and arachidonic acid (AA).

For obtaining an advantageous effect on muscle function, the ω-3 unsaturated fatty acid content is usually at least 10 wt %, preferably at least 15 wt %, based on total lipid content.

In a further embodiment, the composition of the invention comprises stearidonic acid (SDA). Nutritional oils containing SDA are reported to be a dietary source of ω-3 fatty acids that would be more effective in increasing tissue EPA and DPA concentrations than are current ALA-containing oils. Preferably, the lipid fraction in the composition comprises more than 0.5 wt % of SDA, more preferable more than 0.6 wt % of SDA, still more preferably more than 1.2 wt % of SDA, based on total lipid. The maximum amount is more or less limited by the particular source used (type of marine oil), but marine oils with an SDA amount of 2 wt % to about 5 wt % (based on total lipid in the latter oil) are commercially available. Preferably, the amount of SDA in the lipid fraction ranges between 0.5 and 5 wt %, based on total lipid. It is preferred that the amount of SDA is relatively high compared to that of docosahexaenoic acid (DHA) and/or linoleic acid (LA). This allows a high efficacy and manufacture of palatable products comprising low amounts of oxidized products. In effective embodiments of the product according the invention the weight ratio of SDA to DHA is therefore at least 0.22, preferably at least 0.25, more preferably at least 0.30.

A composition of the invention may in particular be a composition wherein at least 55 wt % of the lipid fraction, preferably triglyceride oils, comprise at least 4 wt % of one or more of eicosapentaenoic acid and docosahexaenoic acid.

In a composition of the invention, the lipid fraction comprises less than 30 wt % of a saturated fatty acid, preferably less than 22 wt %, based on total lipid content.

The ratio ω-3 to ω-6 polyunsaturated fatty acids can be chosen within wide limits, e.g. from 0.2 to 10, or from 0.4 to 3.0. In particular, the ratio ω-3 to ω-6 polyunsaturated fatty acids is less than 1.0, preferably 0.97 or less, more preferably 0.95 or less. The ratio is preferably larger 0.5 or more, more preferably 0.6 or more. In particular, preferably the ratio is from 0.5 to 0.97, more preferably from 0.6 to 0.95.

Carbohydrate Fraction

In an embodiment, a composition of the invention comprises a digestible carbohydrate fraction, providing at least 20 en %, preferably at least 30 en % or more preferably at least 38 en % of the total composition.

The digestible carbohydrate fraction in a composition of the invention usually provides 70 en % or less, preferably 60 en % or less, more preferably 48 en % of the total composition.

With the term 'digestible carbohydrate' fraction is meant a fraction comprising one or more digestible carbohydrates.

Digestible carbohydrates include maltodextrose, maltose and glucose. In particular, a carbohydrate is considered digestible in case more than 90% of quickly carbohydrates are digested within 20 min in accordance with the Enquist method.

Especially the composition of the carbohydrate fraction may be chosen to achieve a favourable carbohydrate uptake, and accordingly a desirable insulin release after intake. Accordingly, in particular a composition meeting one or more of the following criteria with respect to the carbohydrate content are considered to be advantageous.

In an embodiment less than 75 wt % of the carbohydrates is formed by the sum of the sucrose and the maltodextrin content.

In an embodiment at least 40 wt % based on the total weight of the carbohydrates is formed by slowly digestible carbohydrates, i.e. in particular carbohydrates which are digested less fast than maltodextrose, maltose and glucose In an embodiment a composition according to the invention comprises less than 60 wt %, preferably 20 to 50 wt % based on the total weight of the carbohydrates of quickly digestible carbohydrates, in particular of maltodextrose, maltose, glucose and other carbohydrates which are digested at least as fast.

In an embodiment more than 20 wt % based on the total weight of the carbohydrates is formed by at least one disaccharide, preferably 22 to 60 wt %. In particular, in such an embodiment, the disaccharide is preferably selected from the group consisting of sucrose, trehalose, palatinose, lactose and other low glycemic disaccharides, more preferably from trehalose and palatinose.

In an embodiment at least one monosaccharide other than glucose is present. Preferably said monosaccharide is selected from the group consisting of galactose, mannose and ribose. Preferably the total amount of said monosaccharide(s) is 0.5 to 30 wt %, more preferably 5 to 25 wt % based on the total weight of the carbohydrates.

In particular, the presence of ribose is advantageous, preferably in combination with (endogenous) folic acid, to increase the protein synthesis. It is contemplated that the combination of these two compounds allows an increase in the production of guanosine triphosphate in the mammal, resulting in an increase of the protein synthesis via stimulation of eukaryotic initiation factor 2B, especially in malnourished patients. The folic acid may be provided in one or more of the following forms: free folic acid, folinic acid, formylated folic acid, methylated folic acid, preferably in a reduced form or as a mono- or polyglutamate conjugated derivative. When present, the folic acid content is usually at least 95 μg per 100 kcal carbohydrates, preferably 110 to 400 μg per 100 kcal carbohydrates, more preferably 125 to 300 μg per 100 kcal carbohydrates.

It is contemplated that it is advantageous with respect to improving the muscle function in a mammal, improving daily activity, improving physical performance, providing a better prognosis in terms of extended life-expectancy, improving compliance to an anti-cancer therapy or with respect to improving a quality of life, that the composition has a relatively low glycemic index. Without being bound by theory it is contemplated that a combination or composition according to the invention to having a low glycemic index is advantageous with respect to muscle protein synthesis, and/or muscle strength, because it contributes to a high insulin sensitivity of the muscle. A high insulin sensitivity is considered to be beneficial in that it improves the stimulating effect of insulin on muscle synthesis (insulin stimulation being a trigger for switching on the anabolic signal of muscle).

Accordingly, in a specific embodiment, the composition is a nutritional composition with a low glycemic index. In particular it is considered advantageous that the glycemic index of the composition is below 55, preferably below 45. In practice, the glycemic index will be above zero, and usually be at least 1, in particular at least 5. Details on how to determine the glycemic index of a composition are provided in the Examples, herein below.

The skilled person will be able to formulate a composition with a relatively low glycemic index based on the information disclosed herein and common general knowledge. In particular, by increasing the percentage of carbohydrate that is digested more slowly than glucose or by increasing carbohydrates that provide less glucose moieties per weight than glucose, the glycemic index of a composition (under otherwise the same condition) is decreased. Preferred examples of carbohydrates which are digested more slowly than glucose are isomaltulose, fructose, galactose, lactose, trehalose. Next to that addition of fat and fibre can slow down gastric emptying. Moreover, fibres can form a physical barrier in the intestine, reducing absorption rate. Amino acids from protein can increase insulin release (especially leucine), and thereby increase glucose uptake by the cells. All these mechanisms can contribute to a reduction in glycemic index.

Indigestible Carbohydrate Fraction

In an embodiment, a composition of the invention comprises an indigestible carbohydrate fraction, In a preferred composition, the indigestible carbohydrate is selected from the group of galactooligosaccharides and fructooligosaccharides.

In particular, the galactooligosaccharide is selected from the group of short-chain galactooligosaccharides, long-chain galactooligosaccharides, or any combination thereof.

In particular, the fructooligosaccharide is selected from the group of short-chain fructooligosaccharides, long-chain fructooligosaccharides, or any combination thereof.

A preferred composition comprises a galactooligosaccharide and a fructooligosaccharide.

Preferably, the molar ratio of galactooligosaccharide to fructooligosaccharide ranges from 1:1 to 20:1, preferably from 5:1 to 12:1, and is most preferably equal to about 9:1.

With an oligosaccharide is meant a chain comprising 2 to 25 saccharide residues.

With a long chain oligosaccharide is meant an oligosaccharide chain comprising 10-25 saccharide residues. With a short chain oligosaccharide is meant an oligosaccharide chain comprising 2-9 saccharide residues, for example 2-5 residues or 6-9 residues.

Indigestible carbohydrates are carbohydrates that remain in essence undigested in the human intestines. In particular, a carbohydrate is considered indigestible in case less than 10% of the sugars is released within 20 and 120 min in an analysis setting using standard digestive enzymes, as determinable by the Enquist method.

In a particular embodiment, the indigestible carbohydrate is selected from the group of galactomannans having a degree of polymerisation (DP) between 2 and 50, xylans with a DP of 2 to 60, oligomers having more than 30 wt % of galacturonic acid or glucuronic acid moieties having a molecular weight of 520 to 2200 Dalton, and any combination thereof.

In an embodiment, the indigestible carbohydrate content is at least 1 wt %, at least 2 wt % or at least 3 wt %, based on total dry matter. In an embodiment, the indigestible carbohydrate content amounts 1 to 15 wt %, preferably 2 to 12 wt %, more preferably 3 to 10 wt %, based on total dry matter.

In a specific embodiment of the present invention, the composition according to the invention may comprise a mixture of neutral and acid oligosaccharides as disclosed in WO 2005/039597 (N. V. Nutricia), which is incorporated herein by reference in its entirety. More in particular, the acid oligosaccharide has a degree of polymerization (DP) between 2 and 5000, preferably between 2 and 1000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day, even more between 0.5 and 20 gram per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, -D-galactopyranose, ribose, glucose, xylose and derivatives thereof, calculated on the total number of monose units contained therein. Suitable neutral oligosaccharides are preferably fermented by the gut flora. Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxohexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4)   α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactose I, II and III), fructans—Levan-type (β-D-(2→6)-fructofuranosyl)$_n$ α-D-glucopyranoside), fructans— Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosacchararides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin, alginate, and mixtures thereof; and a neutral oligosaccharide, selected from the group of fructans, fructooligosaccharides, indigestible dextrins, galactooligosaccharides including transgalactooligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect.

Preferably the composition according to the invention comprises:

an acid oligosaccharides as defined above;

a galactose-based neutral oligosaccharide (of which more than 50% of the monose units are galactose units), preferably selected from the group consisting of galactooligosaccharide and transgalactooligosaccharide; and a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

A mixture of acid- and neutral oligosaccharides is preferably administered in an amount of between 10 mg and 100 gram per day, preferably between 100 mg and 25 grams per day, even more preferably between 0.5 and 20 gram per day.

Nutritional Composition

With a nutritional composition is meant a composition that comprises naturally occurring components, preferably found in the food supply, that can be sold over the counter, as supplements, functional foods or food ingredients i.e. without a physician's or veterinarian's prescription. A nutritional composition may also be a medical food, intended for the dietary management of a disease or condition for mammals under the supervision of a physician or veterinarian.

A composition according to the invention may be in the form of a liquid, e.g. a drink, in the form of a semi-liquid, e.g. a yoghurt or a custard, in the form of a gel, e.g. jelly cake or in the form of a solid, e.g. a candy bar or an ice-cream.

In an embodiment, a liquid composition is prepared from a concentrate, e.g. from a liquid (e.g. with a viscosity of less than about 80 mPa·s), a semi-liquid (e.g. with a viscosity of more than about 80 mPa·s and less than about 400 mPa·s), a gel or a solid. For such preparation, water may be used to dilute the concentrate. In particular, such preparation occurs just before administration of the composition, e.g. in an instant-fashion.

One particular embodiment of the invention is a nutritional composition comprising proteinaceous matter, a lipid, and a digestible carbohydrate, wherein a) the proteinaceous matter content provides 18 to 60 en %, in particular 18 to 50 en %, preferably 20 to 40 en %, more preferably 22 to 32 en % of the total composition, said proteinaceous matter comprising whey;
b) the lipid content provides 10 to 50 en %, preferably 20 to 40 en %, more preferably 25 to 35 en % of the total composition;
c) the digestible carbohydrate content provides 20 to 70 en %, preferably 30 to 60 en %, more preferably 38 to 48 en % of the total composition.

The total energetic value of a liquid composition in accordance with the invention may be chosen within wide limits, e.g. from 0.2 to 4 kcal/ml. Usually it is at least 0.3 kcal/ml, in particular at least 0.8 kcal/ml, more in particular at least 1.2 kcal/ml. Usually, it is 3.0 kcal/ml or less, in particular 2.6 kcal/ml or less, more in particular 2.4 kcal/ml or less. In a specific embodiment, the liquid composition in accordance with the invention has an energetic value in the range of 0.3 to 3.0 kcal/ml, preferably 0.8 to 2.6 kcal/ml, more preferably 1.2 to 2.4 kcal/ml.

In another specific embodiment, the liquid composition in accordance with the invention has an energetic value in the range of 0.2 to 1.0 kcal/ml, preferably 0.4 to 0.9 kcal/ml.

Factors that play a role in determining a desirable energetic value include the ease of achieving a higher en % proteinaceous matter on the one hand and a fast emptying of the stomach (increasing anabolic response) on the other hand.

The total energetic value of a semi-liquid, gel or solid composition in accordance with the invention may be chosen within wide limits, e.g. from 1 to 15 kcal/g. Usually, it is at least 2.0 kcal/g, preferably at least 2.8 kcal/g, even more preferably at least 3.2 kcal/g. Usually, it is 12 kcal/g or less, preferably 10 kcal/g or less, even more preferably 8.0 kcal/g or less. In a specific embodiment, the semi-liquid, gel or solid composition in accordance with the invention has an energetic value in the range of 3.2 to 8.0 kcal/g.

Additional Components

In an embodiment, the composition may comprise one or more other additional components such as at least one component selected from the group consisting of minerals, trace elements and vitamins, preferably selected from the group consisting of sodium, potassium, chloride, fluoride, iodide, calcium, phosphorous, magnesium, vitamin A, vitamin D3, vitamin E, vitamin K, vitamin B1, vitamin B2, vitamin B3, vitamin B5, vitamin B6, folic acid, vitamin B12, biotin, vitamin C, lipoic acid, zinc, iron, copper, manganese, molybdenum selenium and chromium.

Such components may be present in a concentration up to the daily recommended dose per daily serving.

Zinc is preferably present in a concentration of at least 2.8 mg per 100 kcal carbohydrates, more preferably of 5.6 to 20 mg per 100 kcal carbohydrates, even more preferably of 6-15 mg per 100 kcal carbohydrates.

Sustained Release Preparation

In a preferred embodiment, the composition in accordance with the invention further comprises a sustained release preparation effective to release an amino acid in the duodenum and/or the ileum, said preparation comprising at least one component selected from the group consisting of amino acids in the form of a free acid, amino acids in the form of a salt and amino acids in the form of a conjugate with a conjugating compound other than a protein which conjugate is capable of being split in the free amino acid (or salt thereof) and the conjugating compound under the influence of a bile constituent and/or a pancreas excrements in duodenum and/or the ileum.

The amino acid in the sustained release form is preferably suspended in a liquid, semi-liquid or solid product.

The sustained release preparation can be made based upon conventional techniques. The amino acid(s) may be coated with a pH sensitive material that dissolves at the pH existing in the duodenum/ileum (about pH 7) but not in the stomach (strongly acidic). Such coatings are generally known in the art. Examples of conjugating molecules are molecules forming specific peptides with the amino acid that are not split by pepsin, or at least not efficiently split under physiological conditions. Examples are choline, betain, dimethylglycine and sarcosine. Other suitable conjugating molecules include phospholipids, lyso-phospholipids and glycerol.

Amino acids that are preferably present in the sustained release preparation are preferably selected from leucine and other essential amino acids, in particular methionine, arginine, tryptophan, phenylalanine and lysine, of which leucine is especially preferred.

In an advantageous embodiment, a composition according to the invention is administered in a drug regimen. In particular, the composition can be used as adjuvant of a drug, such as a drug selected from the group consisting of anti-cancer drugs, anti-retroviral drugs, antihypertensives, anti-thrombotics, anti-depressants and anti-diabetic drugs. In particular, it is advantageous to use the product with metformin or another anti-diabetic drug. These drugs in particular are considered to be stable in a composition according the invention and to be very effective. Said drug may be present in the composition according to the invention or be administered separately.

The invention further relates to a method for improving the muscle function of a mammal, comprising administering a nutritional composition comprising at least 18 en % of proteinaceous matter having a leucine content of at least 9.5 wt % based on total proteinaceous matter, a lipid fraction comprising at least one ω-3-polyunsaturated fatty acid selected from the group of eicosapentaenoic acid (EPA), docosahexaenoic acid (DHA), eicosatetraenoic acid (ETA) and docosapentaenoic acid (DPA).

The compositions of the invention may be administered under the supervision of a medical specialist, or may be self-administered.

The composition may be administered enterally or orally.

The mammal preferably is a human.

The invention will now be illustrated on the basis of the following examples.

DESCRIPTION OF THE FIGURES

FIG. 1: Differences in A) muscle Tibialis Anterior mass and B) Epididymal fat mass after different interventions Con=mice receiving control diet A (AIN93), TB-con=tumor-bearing mice receiving control diet A (AIN93), hpr=high protein, leu=leucine, fo=fish oil. Data are means±SEM: * sign. different from TB-con (p<0.02) (k=5, α=10%) (For more details about statistics, see the Materials and Methods).

FIG. 2. Skeletal muscle function: force frequency curve (ex-vivo).

CON=mice receiving control diet B, TB-CON=tumor-bearing mice receiving control diet B, TB-SNC=tumor-bearing mice receiving the specific nutritional combination.

Data are means±SEM; data were significantly different from TB-CON when p<0.05 (k=2, α=10%).

A: Maximal contraction force (complete curves significantly different from each other p<0.01).

B. Maximal contraction velocity (complete curves significantly different from each other p<0.01).

C. Maximal relaxation velocity (complete curves significantly different from each other p<0.01).

D. CT90: time needed for contraction from 10 to 90% of maximal force (CON significantly different from TB-CON for range 83-176 Hz; TB-SNC significantly different from TB-CON for range 83-100 Hz).

FIG. 3. Skeletal muscle function during exercise (ex-vivo).

CON=mice receiving control diet B, TB-CON=tumor-bearing mice receiving control diet B, TB-SNC=tumor-bearing receiving the specific nutritional combination. Data as means+/−SEM, Data were significantly different from TB-CON when p<0.05, k=2, α=10%)

A: Maximal contraction force (both curves significant different from TB-CON till repeat 70).

B: Maximal contraction force corrected for muscle mass (CON significant different from TB-CON for repeats 30-50; TB-SNC not significant different from TB-CON).

C: Maximal contraction velocity (both curves significant different from TB-CON till repeat 70).

D: Maximal contraction velocity corrected for muscle mass (CON significantly different from TB-CON for the first 30 repeats (except for repeat 5 (p=0.06)); TB-SNC significantly different from TB-CON for the first 10 repeats).

FIG. 4. Total daily activity.

A: Total daily activity as % of daily activity on day 2 for all groups. A significant time x group interaction was observed (P<0.01).

B: Total activity in the dark as % of daily activity on day 2 for all groups.

C: Total activity in the light as % of daily activity on day 2 for all groups.

A-C: * P<0.05 vs TB-CON

D: Actogram, representing percentages of daily activity during the light period from 7-19 h (white shaded areas) and during the dark period from 19-7 h (grey shaded areas) on days 1-19 (vertical) for all groups separately.

Figure 5:
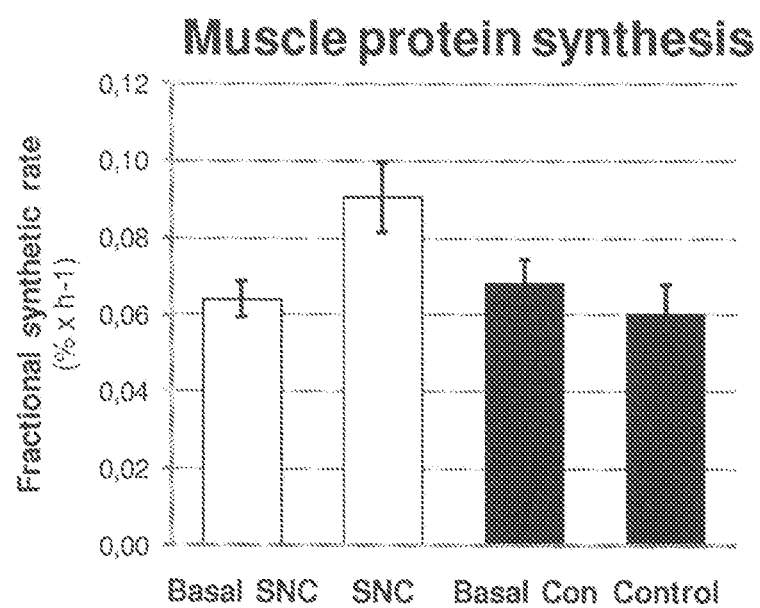
FIG. 5 depicts muscle protein synthesis in colorectal cancer patients.

FIG. 5. Muscle protein synthesis in colorectal cancer patients.

Synthesis is expressed as fractional synthetic rate in stage IV colorectal cancer patients receiving either a specific nutritional combination (SNC) or a control nutritional supplement. Fractional synthetic rate was measured at baseline (basal) and after supplementation.

Figure 6:
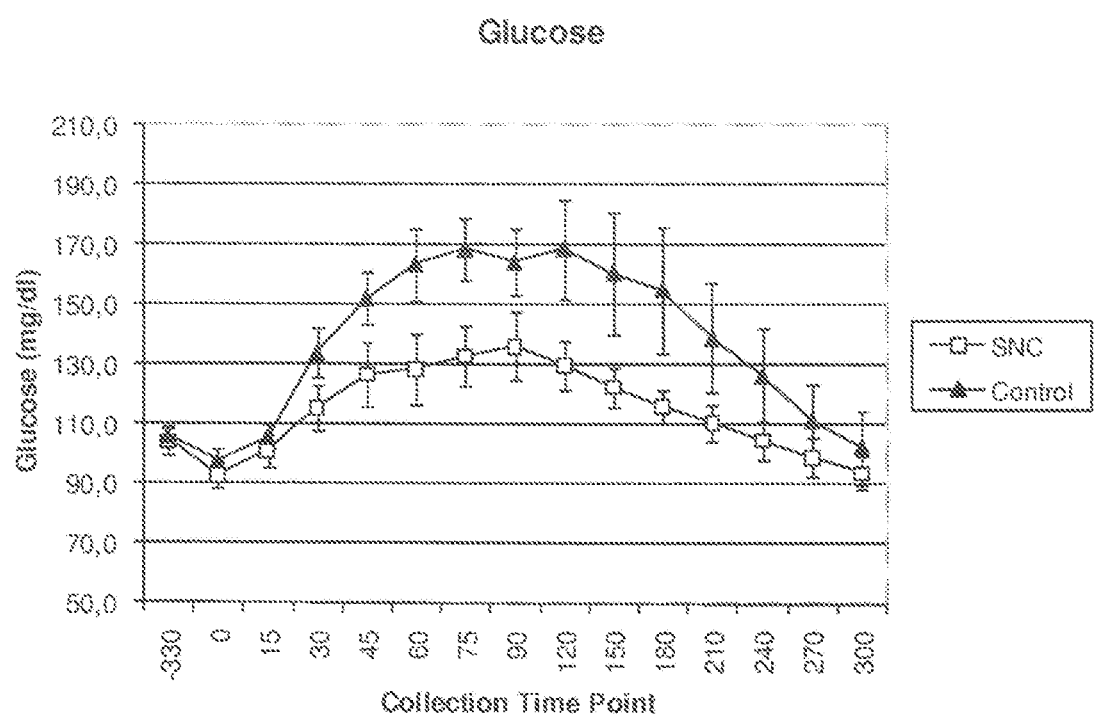
FIG. 6 graphically depicts plasma glucose levels of patients receiving either the specific nutritional combination (SNC) or the control product.

FIG. 6. Plasma glucose levels of patients receiving either the specific nutritional combination (SNC) or the control product.

EXAMPLES

Example 1

Materials and Methods

Animals.

Male CD2F1 mice at 6-7 weeks of age, (BALB/cxDBA/2, Harlan/Charles River the Netherlands) were individually housed in a climate-controlled room (12:12 dark-light cycle with a constant room temperature of 21±1° C.). After acclimatization for one week mice were divided into weight-matched groups: (1) control receiving control chow, (2) tumor-bearing receiving control chow, and (3) tumor-bearing receiving experimental diets. Data shown are derived from the combination of several experimental runs with identical animal characteristics and experimental procedures (unless stated otherwise) and differ only in the experimental diets used. All experimental procedures were approved by the Animal Ethical Committee (DEC consult, Bilthoven, The Netherlands) and complied with the principles of good laboratory animal care.

Experimental Diets (Categories A and B Experiments).

Experiments are divided in: (A) experiments designed to test the effect of single or combinations of nutritional components (addition of high protein (hpr), leucine (leu), fish oil (fo)), added to the background diet (AIN93-M) and supplied as pellets; (B) experiments designed to test the effect of a complex nutritional combination that resembles the composition of Table 3 and comprises all individual components tested in (A), and differing in macronutrient composition from AIN-93 to achieve a more humanized Western-type diet, supplied as a dough for product technical reasons.

The AIN93-M control diet in the category A experiments contained per kg feed: 126 g protein (100% casein), 727 g carbohydrates and 40 g fat (100% soy oil) (Research Diet Services, Wijk bij Duurstede, the Netherlands). Experimental diets in this category were adjusted to control diets by partly replacing the carbohydrates and/or soy oil by protein and leucine (151 g casein/kg and 16 g leucine/kg feed; TB+hpr+leu), high protein and fish oil (151 g casein/kg and 22 g fish oil/kg feed; TB+hpr+fo), or high protein and leucine and fish oil (151 g casein/kg, 15 g leucine/kg and 22 g fish oil/kg food; TB+hpr+leu+fo). The 22 g fish oil contained 6.9 g EPA and 3.1 g DHA resulting in a ratio of 2.2:1.

In the category B experiment, the control diet was iso-caloric and iso-nitrogenous to the control diet in the A-category of experiments and contained per kg feed 126 g protein (casein), 53 g fat (corn oil), and 699 g carbohydrates. The iso-caloric experimental diet (further referred to as Specific Nutritional Composition; SNC) contained per kg feed: 210 g protein (189 g intact protein of which 68% casein and 32% whey and 21 g free leucine), 53 g fat (20.1 g corn oil, 10.2 g canola oil, and 22.2 g fish oil), 561 g carbohydrates, 18 g galacto-oligosaccharides and 2 g fructo-oligosaccharides.

Tumor Model.

Murine C-26 adenocarcinoma cells were cultured in vitro with RPMI 1640 supplemented with 5% fetal calf serum and 1% penicillin-streptomycin. Tumor cells were trypsinized in a sub-confluent state and, after washing, suspended in Hanks' balanced salt solution (HBSS) at a concentration of $2.5 \times 10^6$ cells·mL$^{-1}$. Under general anesthesia (isoflurane/N$_2$O/O$_2$), tumor cells ($5 \times 10^5$ cells in 0.2 mL) were inoculated subcutaneously into the right inguinal flank of the mice. Control (C) animals received a sham injection with 0.2 mL HBSS.

Experimental Protocol.

Following inoculation of tumor cells or HBSS, body mass, food intake and tumor size (length and width) were measured three times a week. Only in the category B experiment, daily activity in the home cage was monitored. In all experiments, animals were anaesthetized and weighted at day 20 after tumor inoculation. Skeletal muscles (e.g. m. Tibialis Anterior (mTA), m. Gastrocnemius (mG), m. Extensor Digitorum Longus (mEDL) and M. Soleus (mS)), the tumor, spleen, kidneys, liver, epididymal fat, thymus, lungs and heart were dissected and weighed. Carcass mass was calculated by subtracting tumor mass from body mass. In addition, muscle function was tested ex vivo in the category B experiment.

Assessment of Daily Activity.

Physical activity was monitored continuously (24 hours) during the 20-day study period starting at day 2, using activity sensors (dual technology detector DUO 240, Visonic; adapted by R. Visser, NIN, Amsterdam, The Netherlands) that translated individual changes in the infrared pattern caused by movements of the animals into arbitrary activity counts. Sensors were mounted above the home cages and were connected via input ports and interface to a computer equipped with MED-PC IV software for data collection (MED associates, St. Albans, Vt.). Activity was expressed in counts per hour (both for the total 24-hours period, the dark period (active period) and the light period (inactive period)). Activity was calculated for each mouse separately and was expressed relative to its own total activity on day 2, to correct for differences in the individual sensitivity of sensors. The activities of two subsequent days were averaged, to dampen the day to day variability. In order to determine changes in activity pattern throughout the experiment, hourly and dark-light activity were expressed as percentage of total daily activity and translated into an actogram.

Assessment of Muscular Functionality.

Contractile characteristics of the right EDL muscle were assessed ex vivo, as described previously (Gorselink, M., Vaessen, S. F., van der Flier, L. G., Leenders, I., Kegler, D., Caldenhoven, E., van der Beek, E., and van Helvoort, A. Mass-dependent decline of skeletal muscle function in cancer cachexia. Muscle Nerve, 33: 691-693, 2006). Briefly, muscles were allowed to stabilize in the organ bath for 30 min, after which optimal stimulation current and strength were determined. Then force-frequency characteristics (10 to 167 Hz, 250 ms) were determined and after replenishing the organ buffer and a resting period of 5 min, muscles were subjected to an exercise protocol (83 Hz, 250 ms every 1000 ms). This protocol represents a moderate load, comparable with normal daily activity. At the frequency used, complete tetanus of the muscle is reached. Isometric force signals of the force-frequency curve were analyzed for maximal and total force and for maximal contraction and relaxation velocity.

Statistics.

All data are expressed as means±SEM. Statistical analyses were performed using SPSS 15.0 (SPSS Benelux, Gorinchem, the Netherlands). In experiment A different batches of animals were used, therefore, for all parameters it was defined that combination of data was allowed if no interaction between groups and experiments were present. Body composition data, tumor and organ masses on day 20 were compared between groups with analysis of variance (ANOVA) and post-hoc LSD. Differences were considered significant at a p value below $\alpha/k$; in which $\alpha=10\%$ and k=amount of comparisons. For experiment A the p-value had to be below 0.02; for experiment B the p-value had to be below 0.05. Data on food intake, body weight, daily activity, and muscle function that were monitored during the 20 days after inoculation were analyzed by repeated measures ANOVA. To further discriminate the differences between groups, the differences or deltas from the first measurement in the range were calculated. These deltas were compared between groups using ANOVA, with post-hoc LSD for pair-wise comparison between groups. For skeletal muscle function, data of first measurement at day 20 were not similar between groups, therefore further discrimination was performed in a per point analysis ANOVA. Differences were considered significant at a two tailed $p<0.05$.

Results

Effects of Single or Combined Nutritional Components on Parameters of Cachexia.

Figure 1B:
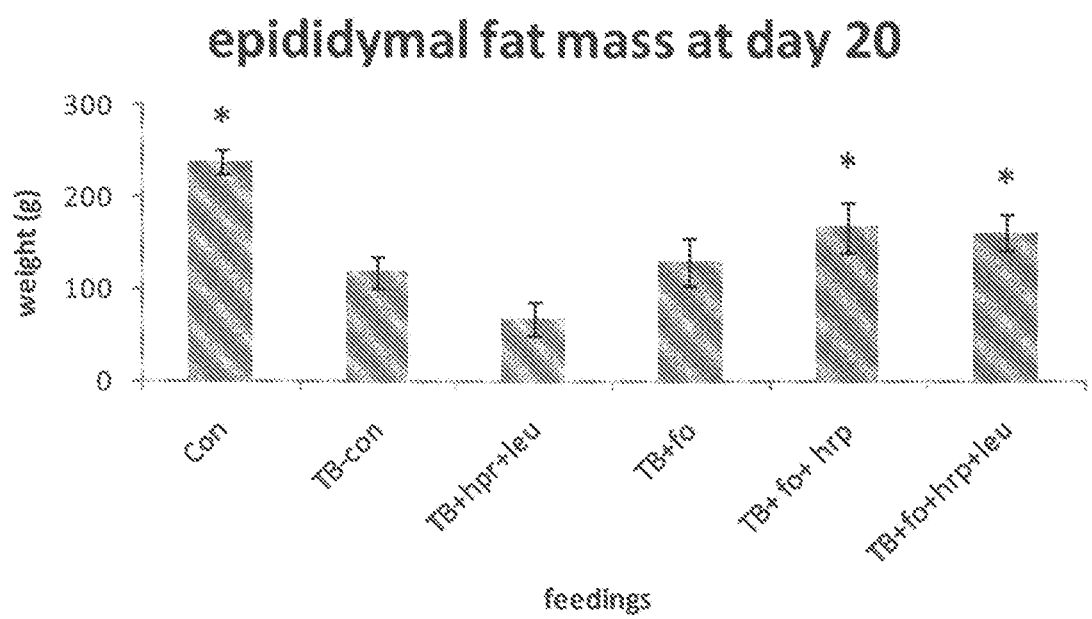

Compared with control mice (Con), carcass and body weight were significantly lower in tumor bearing control mice (TB-con) on day 20 after tumor inoculation (Table 1A). For all parameters measured there was no group * experiment interaction. The loss of body weight in TB-con mice was derived from both loss of fat mass (e.g. epididymal fat) and muscle mass (FIGS. 1A and B). No differences in food intake were present between groups for complete curves. When analyzed separately per day, at day 20, Con was significantly different from TB-con. None of the tumor-bearing groups were significantly different from each other (Table 1B). Addition of extra protein and leucine (TB+hpr+leu) or fish oil (TB+fo) did not change body weight compared to TB-con (Table 1). However, addition of fish oil to extra protein (TB+hpr+fo) or fish oil to extra protein and leucine (TB+hpr+leu+fo), resulted in a significant higher fat mass compared to TB-con (FIG. 1B). Supplementation of the diet with the all-in combination of high protein, leucine and fish oil (TB+hpr+leu+fo) resulted in a significant improvement of body and carcass weight (Table 1A), and of muscle (mTA) and fat (epididymal) mass, compared to TB-con mice (FIG. 1). Additive effects of the combination of leucine and high protein were found for muscle mass of the mTA in the presence of fish oil. Addition of each component increased muscle mass stepwise (FIG. 1A).

TABLE 1

Effect of single or combined nutritional components on body composition, and food intake.

| A body, tumor and carcass weights | | | | | | | |
|---|---|---|---|---|---|---|---|
| treatment | N | CW | p | BW | p | TW | p |
| Con | 40 | 24.4 ± 0.3 | 0.0000* | 24.4 ± 0.3 | 0.001* | 0.0 ± 0.0 | 0.0000* |
| TB-con | 40 | 20.7 ± 0.4 | — | 22.8 ± 0.4 | — | 2.2 ± 0.1 | — |
| TB + hpr + leu | 10 | 20.0 ± 0.6 | 0.8073 | 21.8 ± 0.6 | 0.992 | 1.8 ± 0.1 | 0.1472 |
| TB + fo | 10 | 20.9 ± 0.8 | 0.2264 | 23.0 ± 0.8 | 0.238 | 2.1 ± 0.1 | 0.6854 |
| TB + fo + hpr | 10 | 22.2 ± 0.8 | 0.0337 | 24.2 ± 0.7 | 0.038 | 2.0 ± 0.1 | 0.5053 |
| TB + fo + hpr + leu | 22 | 22.7 ± 0.6 | 0.0099* | 24.4 ± 0.5 | 0.019* | 1.7 ± 0.1 | 0.0659 |

| B food intake (per day) | | | | | | | |
|---|---|---|---|---|---|---|---|
| treatment | N | 1 | 7 | 14 | 17 | 19 | 20 |
| Con | 40 | 4.5 | 3.8 | 4.0 | 3.8 | 3.7 | 3.6* |
| TB-con | 40 | 4.2 | 3.9 | 3.8 | 3.8 | 3.5 | 2.9 |
| TB + hpr + leu | 10 | 4.7 | 3.8 | 4.0 | 3.1 | 3.7 | 2.9 |

TABLE 1-continued

Effect of single or combined nutritional components on body composition, and food intake.

| | | | | | | | |
|---|---|---|---|---|---|---|---|
| TB + fo | 10 | 5.4 | 3.9 | 4.1 | 4.0 | 3.1 | 2.3 |
| TB + fo + hpr | 10 | 4.4 | 3.9 | 3.9 | 3.7 | 3.3 | 2.6 |
| TB + fo + hpr + leu | 22 | 4.4 | 3.5 | 4.1 | 3.5 | 3.4 | 3.0 |

Con = mice receiving control diet A (AIN93),
TB-con = tumor-bearing mice receiving control diet A (AIN93),
hpr = high protein,
leu = leucine,
fo = fish oil,
CW = carcass weight,
BW = body weight, and
TW = tumor weight.
Data as means ± SEM:
*= significantly different from TB-con ($p < 0.02$, $k = 5$, $\alpha = 10\%$), for more details about statistics, see the Materials and Methods.

Effect of a Specific Nutritional Combination on Parameters of Cachexia.

Body and carcass weight were significantly lower in tumor-bearing mice (TB-CON) compared to control mice (CON) on day 20 (Table 2A). The difference in body weight change already being significant at day 15 after tumor inoculation (Table 2C). Again, a significant lower fat mass (epididymal fat) and muscle mass was observed in the TB-CON mice (Table 2B). Food intake was not different between groups (Table 2D). The tumor-bearing mice receiving the Specific Nutritional Combination (TB-SNC group) had a higher body weight, and delta body weight compared to TB-CON mice. The attenuation of body weight loss in the TB-SNC mice coincided with a reduction of fat loss and a reduction in muscle wasting (mTA, mG, and mS) (Table 2B). Organ (wet) mass of kidney, liver, thymus and heart either decreased with increased cachexia or showed no change. Nutritional supplementation resulting in increased carcass weight partly compensated the weight loss. For experiment B, the data for organ masses (in percentage of control (CON)±SEM) were: kidney: TB-CON: 81%±2; TB-SNC: 91%±2, liver TB-CON: 88%±2; TB-SNC: 92%±3, thymus TB-CON: 46%±4; TB-SNC: 55%±4, heart TB-CON: 86%±2; TB-SNC: 88%±2, and lung: TB-CON: 98%±2; TB-SNC: 103%±3. Tumor mass was not increased by any of the nutritional supplementations (Tables 1 and 2).

TABLE 2

Cachexia parameters as a result of an intervention with the specific nutritional combination.

A Body, tumor and carcass weight at section (g at day 20)

| treatment | N | BW | delta BW | TW | CW | delta CW |
|---|---|---|---|---|---|---|
| CON | 10 | 28.0 ± 0.7* | 5.3 ± 0.5* | 0.0 ± 0.0* | 28.0 ± 0.7* | 5.3 ± 0.5* |
| TB-CON | 17 | 20.8 ± 0.5 | −0.7 ± 0.4 | 2.1 ± 0.1 | 18.7 ± 0.4 | −2.8 ± 0.4 |
| TB-SNC | 18 | 23.1 ± 0.6* | 0.9 ± 0.6* | 1.7 ± 0.1* | 21.4 ± 0.6* | −0.7 ± 0.7* |

B Organ weights at section (mg at day 20)

| treatment | N | Epididymal fat | mTA | mG | mEDL | mS |
|---|---|---|---|---|---|---|
| CON | 10 | 443 ± 37* | 44.5 ± 1.3* | 141 ± 4* | 9.2 ± 1.1 | 6.7 ± 0.5* |
| TB-CON | 17 | 87 ± 18 | 33.4 ± 0.9 | 108 ± 2 | 7.8 ± 0.2 | 5.3 ± 0.2 |
| TB-SNC | 18 | 189 ± 20* | 38.1 ± 0.9* | 118 ± 3* | 8.3 ± 0.5 | 5.7 ± 0.2* |

C Change in BW in time

| | | change in BW (change in g: day 0-20 when compared to day −1) | | | | |
|---|---|---|---|---|---|---|
| treatment | N | 0 | 6 | 10 | 15 | 20 |
| CON | 10 | 1.0 ± 0.3 | 3.6 ± 0.4 | 4.3 ± 0.7 | 5.5 ± 1.0* | 6.3 ± 1.4# |
| TB-CON | 17 | 0.6 ± 0.3 | 2.7 ± 0.3 | 3.3 ± 0.3 | 3.7 ± 0.4 | −0.1 ± 0.5 |
| TB-SNC | 18 | 0.9 ± 0.2 | 3.4 ± 0.3 | 4.4 ± 0.4 | 4.6 ± 0.4 | 1.8 ± 0.6# |

D Foodintake in time

| | | Foodintake per day (g) | | | |
|---|---|---|---|---|---|
| treatment | N | 8 | 13 | 17 | 19 |
| CON | 10 | 4.4 ± 0.2 | 4.3 ± 0.2 | 4.4 ± 0.3 | 3.5 ± 0.6 |
| TB-CON | 17 | 4.0 ± 0.2 | 4.1 ± 0.1 | 3.7 ± 0.3 | 3.5 ± 0.5 |
| TB-SNC | 18 | 4.2 ± 0.1 | 4.5 ± 0.2 | 4.8 ± 0.3 | 4.4 ± 0.4 |

CON = mice receiving control diet B,
TB-CON = tumor-bearing mice receiving control diet B,
TB-SNC = tumor-bearing mice receiving the specific nutritional combination.

TABLE 2-continued

Cachexia parameters as a result of an intervention with the specific nutritional combination.

BW = body weight;
delta BW = BW day 20 minus BW day 0,
delta CW = CW day 20 minus CW day 0,
TW = tumor weight,
mTA = muscle Tibialis Anterior,
mG = muscle Gastrocnemius,
mEDL = muscle Extensor Digitorum Longus,
mS = muscle Soleus.
Data as means ± SEM:
*= significantly different from TB-CON ($p < 0.05$, $k = 2$, $\alpha = 10\%$);
= significantly different from TB-CON for the whole curve ($p < 0.05$, $k = 2$, $\alpha = 10\%$).
(For more details about statistics, see the Materials and Methods).

Ex-Vivo Muscle Function (Category B Experiment).

Figure 2A:
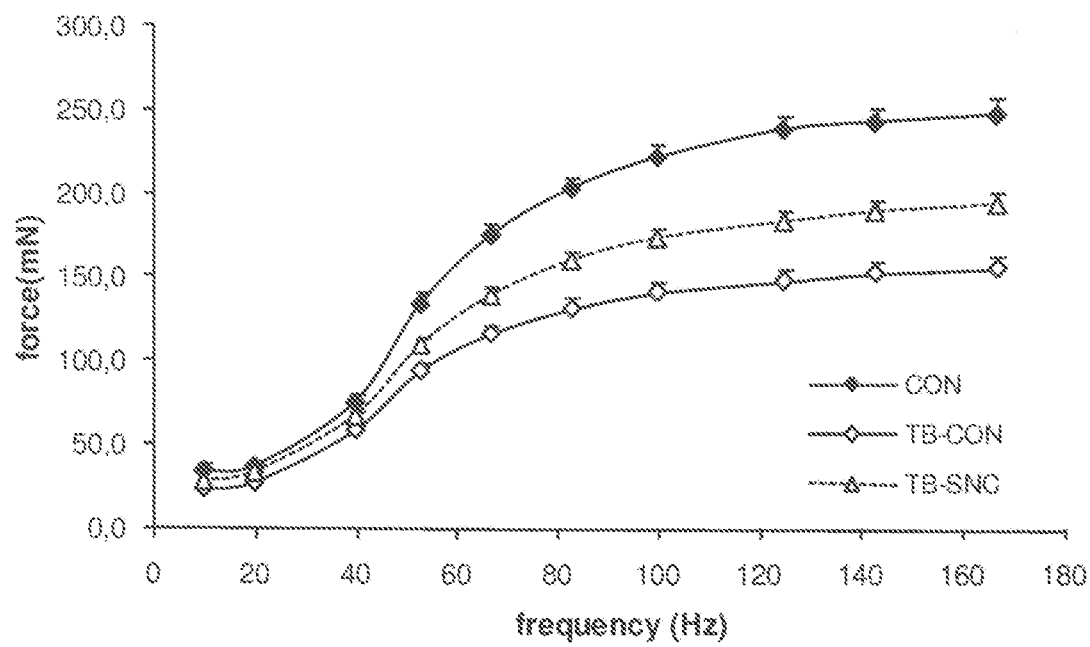
FIGS. 2A, 2B, 2C, and 2D graphically depict the skeletal muscle function: force frequency curve (ex-vivo).
Figure 2B:
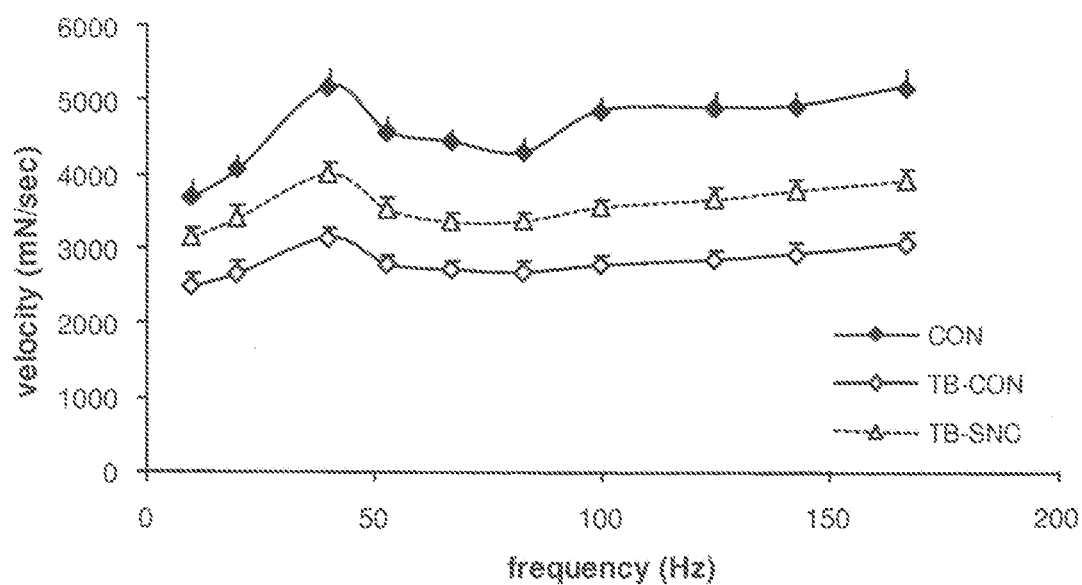
Figure 2C:
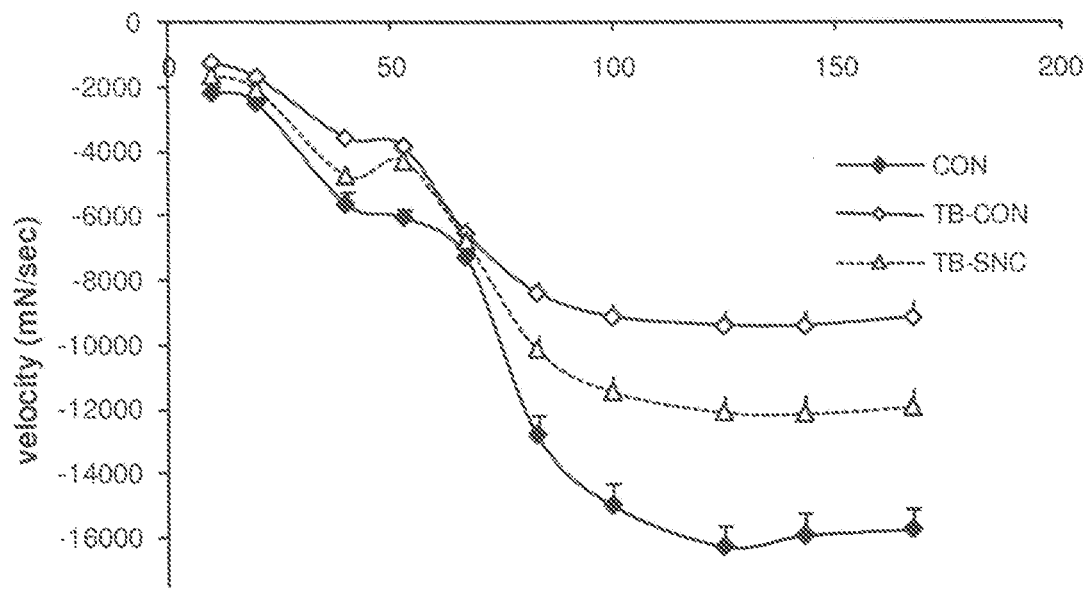
Figure 2D:
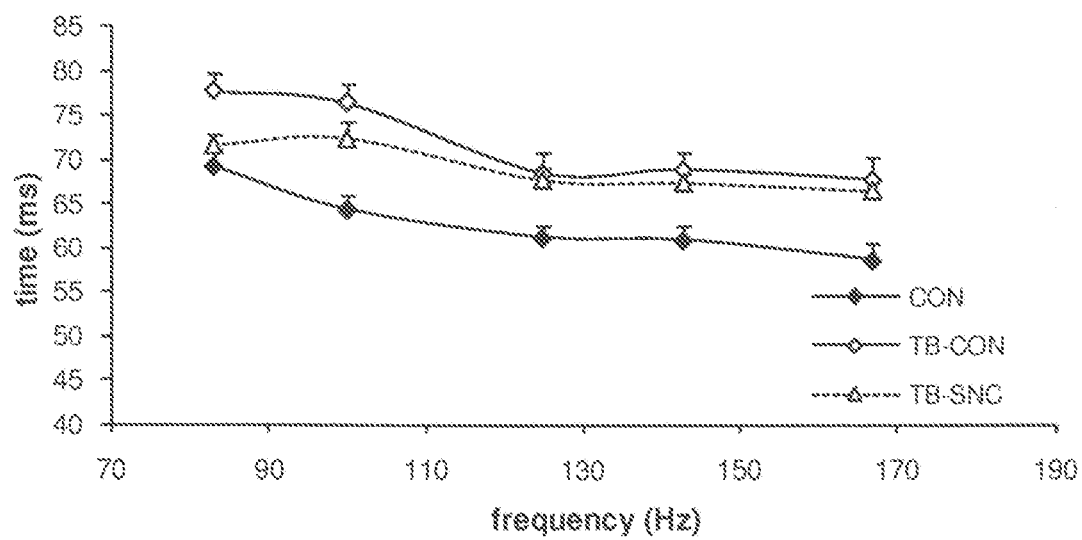
Figure 3A:
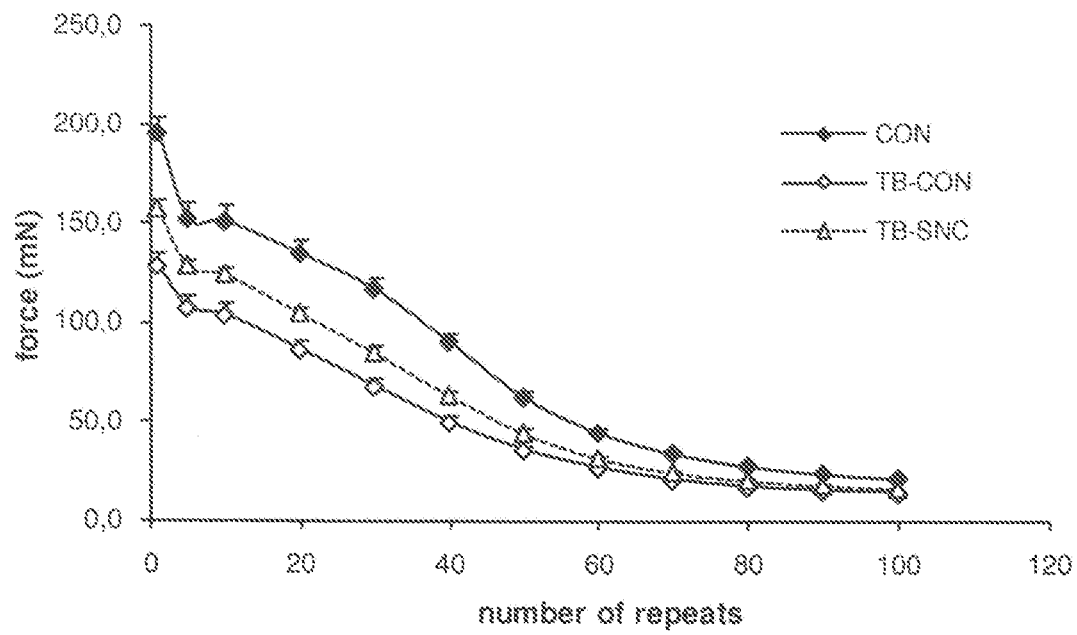
FIGS. 3A, 3B, 3C, and 3D graphically depict the skeletal muscle function during exercise (ex-vivo).
Figure 3B:
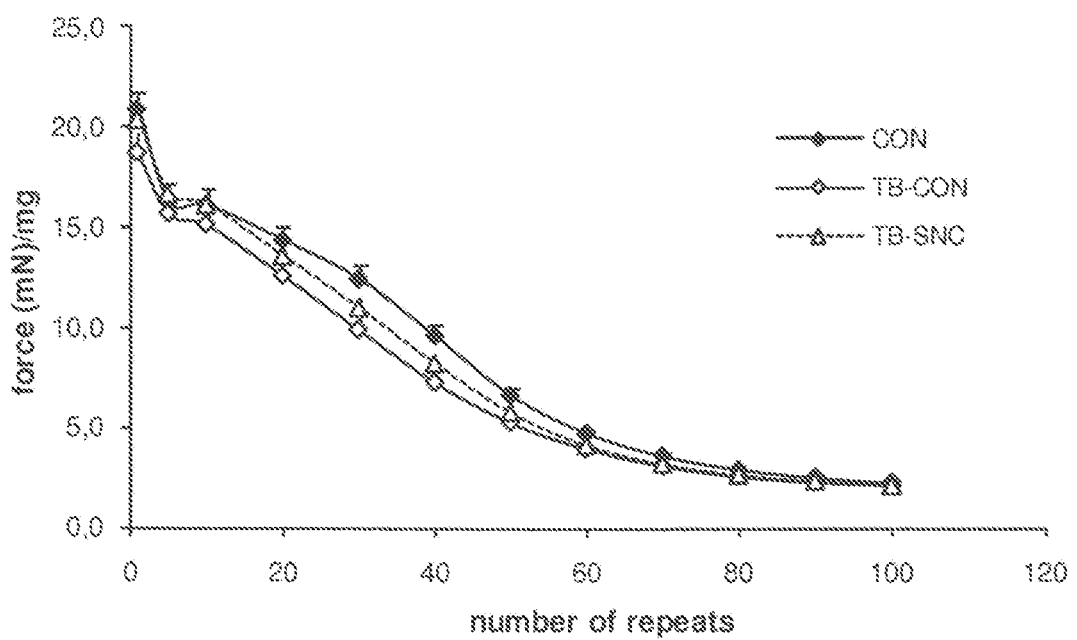
Figure 3C:
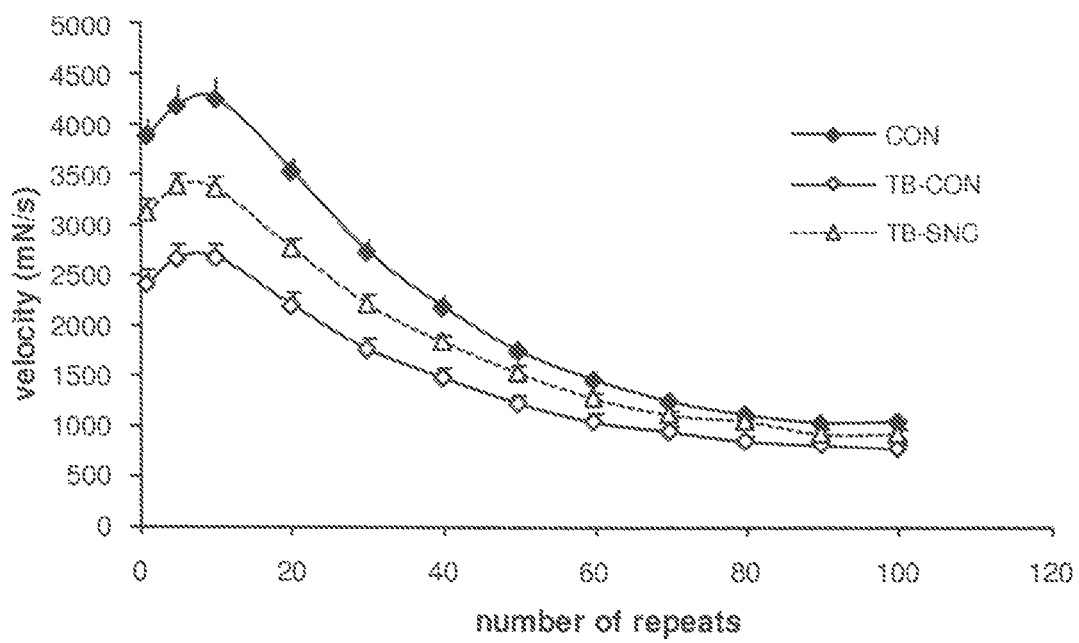
Figure 3D:
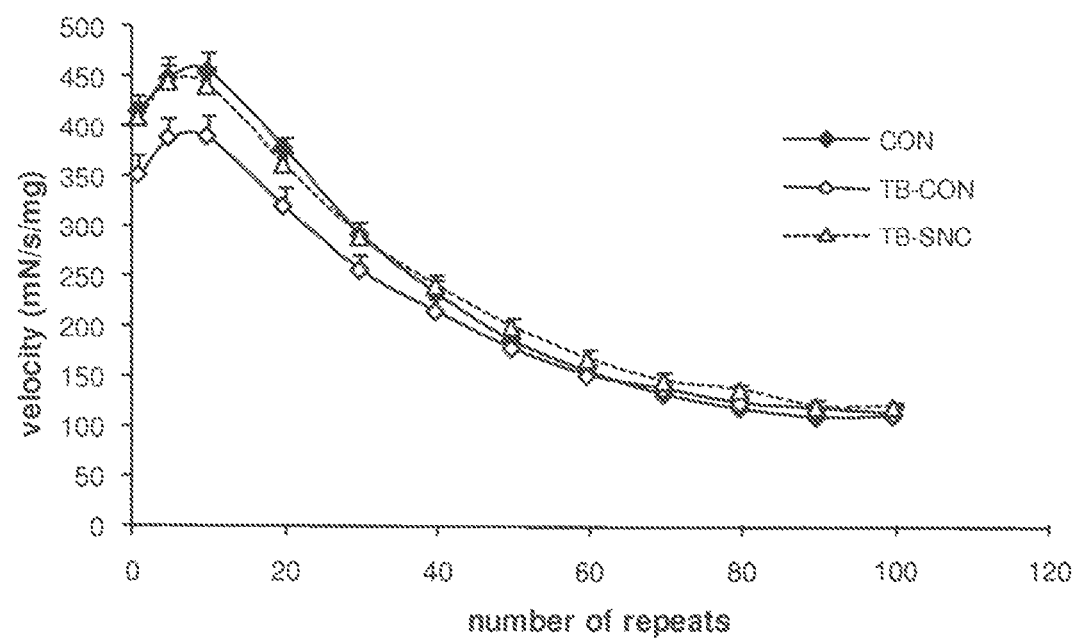

Force-frequency characteristics (10 to 167 Hz, 250 ms) were determined ex vivo in mEDL. Maximal force, maximal contraction velocity and maximal relaxation velocity were significantly different in TB-CON when compared to CON and TB-SNC (FIGS. 2 A, B, and C). When these parameters were corrected for muscle mass, overall curve positions maintained. Significant differences, however, only remained between CON and TB-CON. To further investigate muscle mass-independent changes in muscle function the time needed for a contraction (CT90) was determined. CT90 was defined as the time needed to go from 10 to 90% of maximal contraction force, at frequencies at which tetanus was obtained. CT90 was significantly different between TB-SNC and TB-CON at lower frequencies at which total tetanus could be obtained (83 and 100 Hz). These data suggest that at frequencies (83-100 Hz) relevant for efficient physical performance (tetanus present), besides muscle mass-dependent changes, also muscle mass-independent changes had occurred that were corrected by specific nutritional intervention. Therefore, an exercise protocol of 100 repeated pulses was applied at 83 Hz. Again, CON and TB-SNC were significantly different from TB-CON during the whole exercise protocol for maximal contraction force (FIG. 3A) and maximal contraction velocity (FIG. 3C). When maximal contraction force was corrected for muscle mass (FIG. 3B) curve positions remained, with only significant differences between CON and TB-CON. Maximal contraction velocity of the TB-SNC group, however, was still significantly different from TB-CON when corrected for muscle mass in the first repeats of the exercise (<10 repeats) (FIG. 3D).

Physical Activity (Category B Experiment).

Figure 4A:
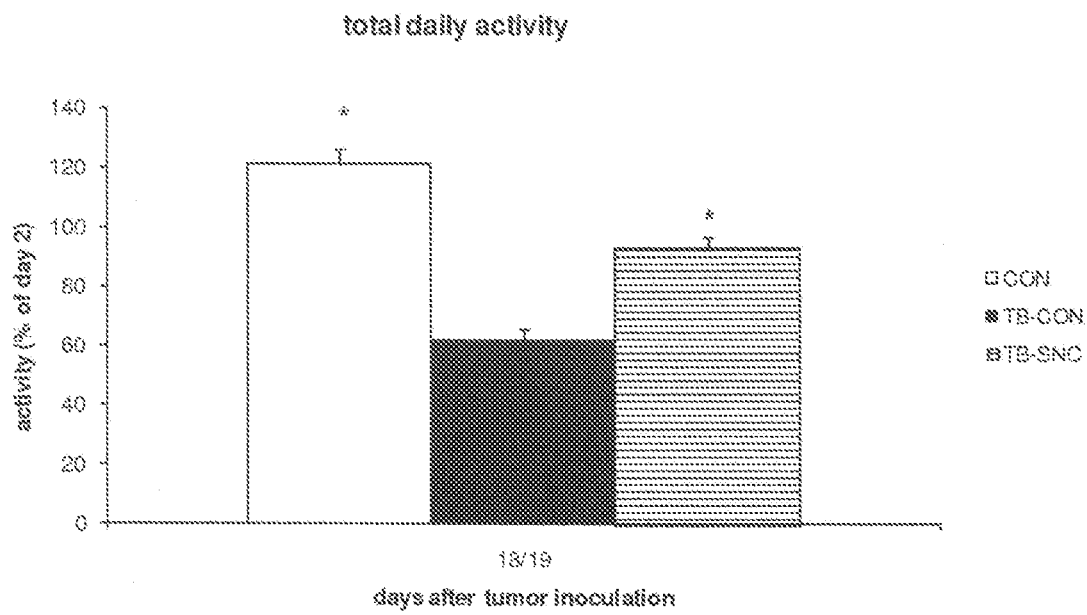
FIGS. 4A, 4B, 4C, and 4D depict total daily activity.
Figure 4B:
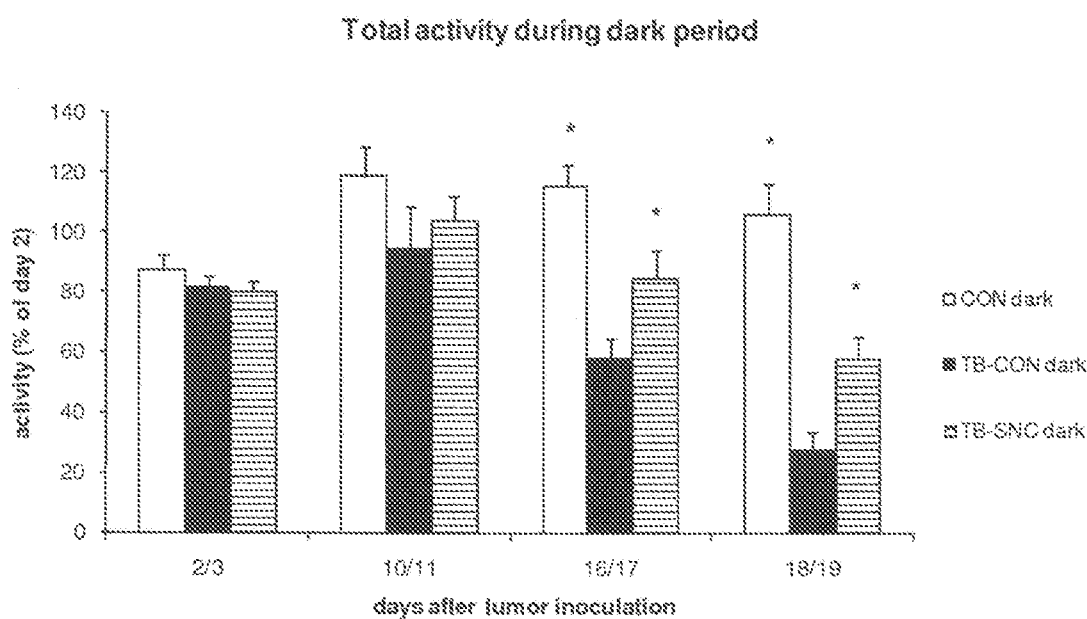

Total daily activity showed a significant interaction between time and group (P<0.01; RM-ANOVA) over the total period (2-19 days). Activity levels in TB-CON mice were significantly lower than in control mice on days 10-11 (P<0.05), and from day 16 onwards (P<0.01). The TB-SNC animals did not differ significantly from the control animals in their total activity throughout the experiment, while their activity was significantly higher at days 18-19 compared with TB-CON mice (P<0.05) (FIG. 4A). These differences in total activity resulted from significant changes during their active period (i.e. dark period) (FIG. 4B). Throughout the dark period, TB-CON mice were significantly less active than controls on days 16-17 and 18-19 (P<0.01), resulting in a drastic decrease in overall activity in the TB-CON mice. The TB-SNC mice were less active than control mice during the dark on day 18-19 (P<0.05), but more active than TB-CON mice on those days (P<0.05).

Figure 4C:
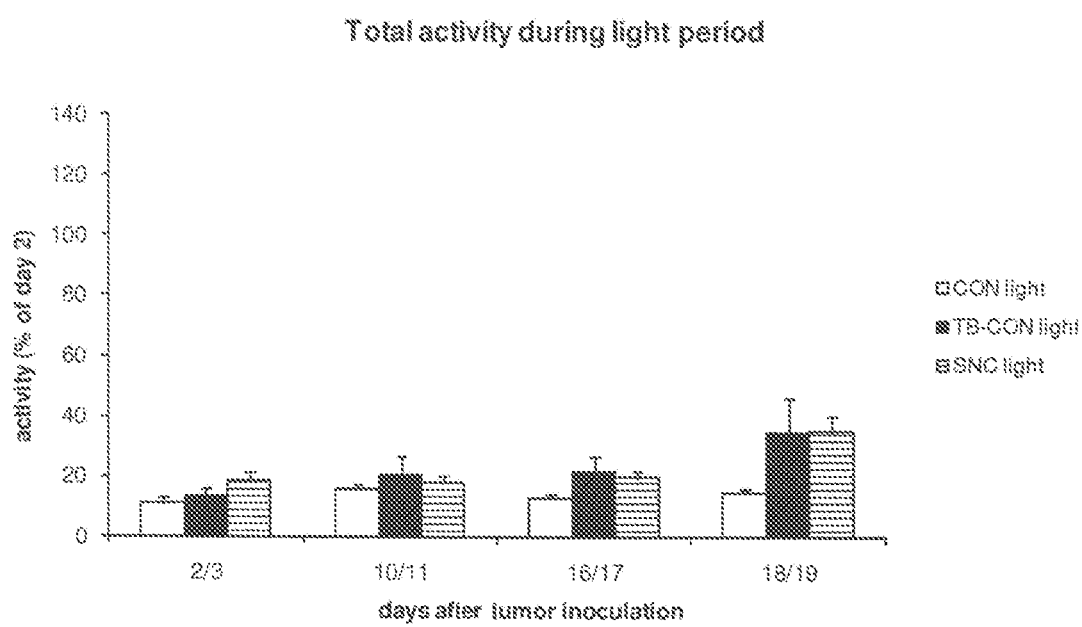
Figure 4D:
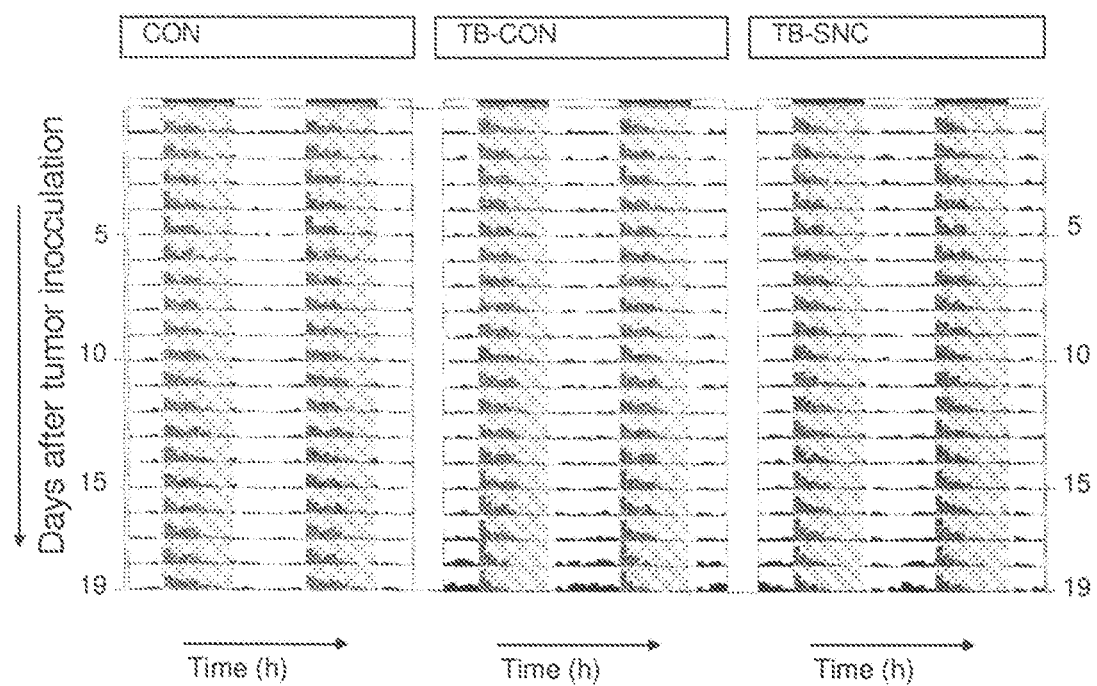

Besides a reduction in daily activity level of TB-CON mice, a clear shift in daily activity pattern was observed, i.e. from dark to light, both in tumor-bearing controls and in TB-SNC animals on days 18-19 (FIG. 4C). To focus on possible shifts in daily activity pattern, hourly activity pattern during the day was expressed as a percentage of the total (100%) daily activity on that specific day (FIG. 4D) (i.e. not referring to day 2 and not corrected for the graduate decline in activity for the tumor-bearing groups). At baseline (days 2-3) all groups showed comparable day/night rhythms. Animals were active during the dark and had an inactive period during the light. A relative shift towards increased activity during the light period is observed in the TB-CON group from day 16, which occurs less or delayed in the TB-SNC group.

Discussion.

The present study comparing nutritional intervention with single and multiple components clearly supports the added value of a multi target approach with specific nutrients on body composition in the murine C26 carcinoma model. In addition, the specific nutritional combination also improved muscle function. Moreover, activity patterns as well as overall daily activity improved, probably as a consequence of improved body composition and muscle function. These findings are highly relevant to the clinical situation, because muscle function and daily activity are important contributors to the quality of life of the cancer patient. Therefore, these data strongly endorse the use of specific nutritional support for cancer patients with a combination of multiple ingredients.

The data focus on the specific nutritional needs of the cancer patient to improve or prevent cachexia characteristics, and show the effects of different isocaloric nutritional interventions with single ingredients or combined nutritional components in the C26 murine model of cancer-induced cachexia. There were no significant differences on food intake between groups on complete curves nor on analysis per day up to day 19. These data confirm earlier findings that the C26 adenocarcinoma mouse model is a cachectic non-anorectic model. The observation, however, that in experiment A, food intake of Con is significantly higher than that of TB mice on day 20 specifically indicates that if tumor growth would continue for a few days more, the tumor bearing animals would likely become anorectic. The differences in cachectic parameters between control and tumor-bearing mice 20 days after tumor inoculation, were comparable in magnitude to those described in other studies also using the C26 adenocarcinoma mouse model.

From the single components only fish oil increased fat mass. Fat mass has been suggested to be important in survival of the patient while muscle mass has been implicated to contribute specifically to the quality of life of the patient. The data on mTA muscle mass show that at the tested concentration the combination of all components, i.e. fish oil, high protein and leucine were needed for a significant effect on muscle mass (FIG. 1). These results are in line with the hypothesis that next to an increase in anabolic responses, protein catabolism has to be decreased via reduction of inflammation to reach a positive effect on muscle protein mass in a cancer cachectic state. There is growing support that the inflammatory response to a tumor attributes considerably to the progression towards cachexia. It has also been suggested that the increase in catabolic vs. anabolic processes contributes to the failure to accumulate lean body mass even when nutritional intake is normal. Clinical data from different cachectic patient groups in the literature suggest that fish oil might reduce catabolism and weight loss. Fish oil probably not only attenuates the tumor-induced inflammatory response, but also normalizes the insulin resistance present in the cachectic state. Prolongation of survival has been reported in a mixed group of advanced cancer patients supplemented with ω-3 fatty acids and vitamin E (Gogos, C. A., Ginopoulos, P., Salsa, B., Apostolidou, E., Zoumbos, N. C., and Kal-farentzos, F. Cancer, 82: 395-402., 1998) which might also result from immune-modulation. The suggestion that in cachectic patients fish oil might contribute to the maintenance of body composition via a reduction of inflammatory responses, is supported by our data. High protein with leucine (hpr+leu), did not result in significant changes in mTA mass. However, when fish oil was added, the combination of high protein and leucine (hpr+leu+fo) contributed to a significant weight gain of mTA. Therefore, it is hypothesized that reduction of the inflammatory state by fish oil improved the sensitivity of the animals to anabolic stimuli like leucine and high protein, resulting in improved maintenance of muscle protein mass.

Results from in vivo studies suggest that BCAAs and especially leucine regulate skeletal muscle protein metabolism (Rooyackers, O. E. and Nair, K. S. Annu Rev Nutr., 17: 457-485., 1997). This signal is related to activation of the mTOR pathway. In healthy volunteers, leucine has been reported to provide a signal for stimulation of muscle protein synthesis and to possibly decrease muscle protein breakdown (Rennie, M. J., Bohe, J., Smith, K., Wackerhage, H., and Greenhaff, P. J. Nutr., 136: 264S-268S., 2006). In healthy individuals this signal is likely to be short-lived due to the 'muscle-full phenomenon' induced by normal nutritional intake and homeostatic control mechanisms. In contrast, long lasting effects of BCAA supplementation were reported in patients with a metabolic or nutritional deficiency like in septic or cancer patients. In these patient groups BCAA supplementation was reported to result in positive effects on albumin status, quality of life and overall survival. Moreover, it has been reported that protein synthesis can only be stimulated in the presence of a high supply of balanced amounts of essential amino acids (Rooyackers, O. E. and Nair, K. S. Annu Rev Nutr., 17: 457-485., 1997). Altogether, these studies suggest that a combination of high protein and BCAA supplementation might result in improved protein metabolism, resulting in muscle mass gain, which could contribute to a lower morbidity and a higher quality of life. Our data indeed suggest that both leucine and high protein supplementation contribute to the cumulative effect on muscle mass maintenance, reached by the total nutritional combination (FIG. 1 and Table 1).

To our surprise, a combination of supplementation of high protein, leucine and fish oil resulted in a surplus value with respect to a broad spectrum of parameters characterizing cachexia. The group in which all nutritional components were combined (TB+hpr+leu+fo mice) was the only group that showed significant differences versus TB on all read-out parameters of cachexia (e.g. weights of body, carcass, muscles and fat (see Table 1). The suggested additive effects of single nutritional components to the total combination are best illustrated by the data on tibialis muscle mass (mTA FIG. 1). These data clearly indicate a surplus value of a multi-nutritional-component approach. We suggest that the observed additive effects originate from presumed differences in mechanistic targets of these components, i.e. 1) stimulation of anabolic signals by supplementation of building blocks (essential amino acids) and by stimulation of mTOR (leucine), 2) reduction of protein catabolism by the reduction of inflammatory and hormonal responses (fish oil) and down regulation of the signaling pathway leading to protein breakdown (leucine), and the possible interaction(s) between these mechanisms. The second experiment confirmed the efficacy of the nutritional combination on body composition maintenance. Moreover, in this experiment the combination of ingredients also improved parameters reflecting physical performance like muscle function and daily activity patterns.

Organ (wet) mass of kidney, liver, intestine, thymus and heart were unaffected or decreased with increased cachexia. Nutritional supplementation resulting in increased carcass weight had no effect or partly normalized the loss in organ mass. Moreover, none of the selected ingredients increased tumor size. The complete nutritional combination showed a reduction in tumor size in experiment B.

C26-tumor inoculation induced a loss of muscle function. A large part of the reduction of muscle function was explained by a reduction in muscle mass. These findings are in accordance with clinical data. Gogos et al reported a significantly higher Karnofsky performance status in malnourished patients supplemented for 40 days with 18 g of ω-3 PUFA compared with placebo (Gogos, C. A., Ginopoulos, P., Salsa, B., Apostolidou, E., Zoumbos, N. C., and Kal-farentzos, F. Cancer, 82: 395-402., 1998.). These data suggest that improvement of physical activity may occur even before a significant weight gain is achieved. This may indicate that for maintaining normal life activities, preventive treatment to reduce muscle wasting is recommended. In our experimental setup, all tumor-induced muscle mass-dependent decreases in muscle function could be significantly restored by supplementation with the specific nutritional combination. These data are supported by clinical trial data of Barber et al. reporting an improved functional performance after 3 and 7 weeks of supplementation with 2.2 g EPA+0.96 g DHA in unrespectable pancreatic cancer patients. The improved physical performance coincided with increased BW and appetite (Barber, M. D., Fearon, K. C., Tisdale, M. J., McMillan, D. C., and Ross, J. A. Nutr Cancer, 40: 118-124, 2001.). Next to muscle mass-dependent changes in muscle function, also muscle mass-independent loss of function is suggested by presented data (FIGS. 2D and 3D). A tumor-related, muscle mass independent decrease in muscle function has not been described before. This compromised muscle function became especially manifest in the maximal contraction velocity after exercise of moderate strength (FIG. 3C). The muscle mass-independent decrease in muscle function could also be partly restored by supplementation with the specific nutritional combination (TB-SNC). These results indicate that the nutritional combination restores both muscle mass dependent and muscle mass independent decreases in muscle function.

Asthenia, resulting from cancer cachexia, leads to a reduced daily activity. Indeed, in the presence of a tumor, daily activity levels of mice decreased over time which is in line with clinical reports of cancer patients. It is not clear what mechanism induces the reduction in activity in cachectic cancer patients. Reduced muscle mass and decreased muscle force may contribute to the deterioration in activity. In addition, the tumor-induced inflammatory response might further reduce the daily activity. Physical activity is a major determinant of quality of life (Moses, A. W., Slater, C., Preston, T., Barber, M. D., and Fearon, K. C. Br J Cancer, 90: 996-1002, 2004). The complete nutritional combination tested maintained activity compared to TB-CON mice. This effect may be directly related to the better maintained physical performance (improved muscle mass and function). The influence of the nutritional combination on other factors involved in physical performance, however, would need further examination.

Chevalier et al. reported that patients with advanced colorectal cancer showed less contrast between day time and night time activity (nocturnal sleep) (Chevalier, V., Mormont, M. C., Cure, H., and Chollet, P. Oncol Rep, 10: 733-737, 2003.). Individual activity patterns have even been suggested to be predictive of the patients' survival, tumor response and quality of life. The possibility of a tumor-induced disturbance in diurnal activity patterns is supported by our data, indicating a tumor-related shift in activity from the dark to the light period. The specific nutritional combination tested shows a clear trend to reduce this effect. Normal sleep patterns are critically dependent on the circadian release of melatonin from the pineal gland. DHA-enriched formulas have been reported to normalize melatonin secretion in (ω-3)-deficient rats (Zaouali-Ajina, M., Gharib, A., Durand, G., Gazzah, N., Claustrat, B., Gharib, C., and Sarda, N. J Nutr, 129: 2074-2080, 1999.); this might also be an explanation for the results obtained in our experiments.

Based on the results from this study, it is clear that more attention should be paid to prevention of cachexia in order to maintain quality of life for the patient.

In conclusion, a nutritional combination of high protein, leucine and fish oil improved the cachectic outcome of mice inoculated with the C26 adenocarcinoma cell line. Not only did the carcass, fat and muscle mass increase, also muscle function and daily activity improved when compared to tumor-bearing mice on the control diet. These data show that single ingredient interventions have limited value, and support the need for a balanced combination of different ingredients to enable a multi-targeted intervention to achieve effects in the complex conditions of cancer cachexia.

Example 2

Formulation Examples

A sip feed may in particular comprise macronutrients in ranges specified in Table 3. A specific example is given in Table 4. In addition one or more micronutrients (such as minerals, vitamins, etc.) and/or one or more other food-grade additives (e.g. flavourings; preservatives; non-proteinogenic amino acids, such as carnitine) may be present.

TABLE 3

Nutritional composition of a Sip Feed (per 100 ml)

| | |
|---|---|
| Proteinaceous matter (equivalent) (g) | 9-12 |
| containing total whey protein | 1-9 |
| containing total leucine (g) | 1.5-2.5 |
| of which Leucine as free amino acid (g) | 0.9-1.5 |

TABLE 3-continued

Nutritional composition of a Sip Feed (per 100 ml)

| | |
|---|---|
| Carbohydrate (g) | 10-25 |
| Fat (g) | 2-6 |
| of which unsaturated | 2-6 |
| of which omega 3 poly unsaturated | 0.8-2 |
| of which EPA, DHA, ETA, DPA | 0.2-2 |
| Soluble fibre, dietary g | 1-4 |

TABLE 4

Nutritional composition of a sip feed (per 100 ml)

| | |
|---|---|
| Proteinaceous matter (equivalent) (g) | 10.1 |
| containing total whey protein | 2.9 |
| containing total leucine (g) | 2.0 |
| of which Leucine as free amino acid (g) | 1.1 |
| Carbohydrate (g) | 17.4 |
| Fat (g) | 5.3 |
| of which unsaturated | 4.2 |
| of which omega 3 poly unsaturated | 1.1 |
| of which EPA, DHA, ETA, DPA | 1.1 |
| Soluble fibre, dietary g | 2.0 |

A tube feed may in particular comprise macronutrients in ranges specified in Table 5. A specific example is given in Table 6. In addition one or more micronutrients (such as minerals, vitamins, etc.) and/or one or more other food-grade additives (e.g. flavourings, preservatives) may be present.

TABLE 5

Nutritional composition of a tube feed

| | |
|---|---|
| Proteinaceous matter (equivalent) (g) | 6-10 |
| containing total whey protein | 1-8 |
| containing total leucine (g) | 1-2 |
| of which Leucine as free amino acid (g) | 0.4-0.9 |
| Carbohydrate (g) | 10-25 |
| Fat (g) | 2-6 |
| of which unsaturated | 2-6 |
| of which omega 3 poly unsaturated | 0.4-1 |
| of which EPA, DHA, ETA, DPA | 0.1-1 |
| Soluble fibre, dietary g | 1-4 |

TABLE 6

Nutritional composition of a tube feed

| | |
|---|---|
| Proteinaceous matter (equivalent) (g) | 7.8 |
| containing total whey protein | 2.9 |
| containing total leucine (g) | 1.5 |
| of which Leucine as free amino acid (g) | 0.8 |
| Carbohydrate (g) | 17.2 |
| Fat (g) | 5.4 |
| of which unsaturated | 4.5 |
| of which omega 3 poly unsaturated | 0.8 |
| of which EPA, DHA, ETA, DPA | 0.7 |
| Soluble fibre, dietary g | 1.5 |

The following composition (Table 7) was made according to standard procedures and is suitable for use according to the invention, preferably as a sip feed.

TABLE 7

Main ingredients of a specific composition according to the invention

| INGREDIENTS | AMOUNT |
|---|---|
| Energy content | 160 kcal/100 ml |
| Protein (27 en %) | 10.1 g/100 ml of which: |
| | whey: 2.9 g/100 ml |
| | casein: 6.1 g/100 ml |
| | added leucine: 1.1 g/100 ml |
| | wherein the following amino acids are present (based on total protein weight): |
| | L-Leucine: 19.4 wt % |
| | L-Glutamine/Glutamic acid: 17.8 wt % |
| | L-Cysteine: 0.9 wt % |
| | Lysine: 7.5 wt % |
| | leu/(val + ile) – ratio = 1.83 |
| Carbohydrates (43 en %) | 17.4 g/100 ml of which: |
| | sugar blend comprising glucose, galactose, lactose, maltose, sucrose and trehalose (12.7 g/100 ml) |
| | starch (4.3 g/100 ml) |
| Lipids (30 en %) | 5.3 g/100 ml of which: |
| | ω-3 |
| | ALA (1.8 g/100 g of total lipid) |
| | EPA (11.9 g/100 g of total lipid) |
| | DHA (5.8 g/100 g of total lipid) |
| | DPA (1.4 g/100 g of total lipid) |
| | SDA (1.8 g/100 g of total lipid) |
| | ω-6 |
| | LA (26.0 g/100 g of total lipid) |
| | AA (0.7 g/100 g of total lipid) |
| | ω-3/ω-6 = 0.87 |
| Others: | |
| Dietary fiber | 2 g/100 ml of galactooligosaccharides |
| L-carnitine | 10.9 mg/100 ml |
| Taurine | 13.2 mg/100 ml |
| Viscosity | 41 mPa · s |

Example 3

Muscle Protein Synthesis after Nutritional Supplementation in Colorectal Cancer Patients A sip feed containing a specific nutritional combination as described in Table 4 from the possible compositions was tested on its capacity to influence muscle protein synthesis rate and compared to a control product as described in Table 8.

TABLE 8

Supplements Composition

| | Specific Nutritional Combination (SNC) (100 ML) | | CONTROL (100 ML) | |
|---|---|---|---|---|
| Energy | Kcal | 160 | Energy | Kcal | 160 |
| Protein* | g | 10.1 g | Protein* | g | 6.0 |
| Fat | g | 5.3 | Fat | g | 5.8 |
| Carbohydrates | g | 17.4 | Carbohydrates | g | 21.0 |

*SNC: 2.9 g whey protein, 1.1 g free leucine, balance casein; control only casein Research Design and Methods Study Subjects.

Subjects were enrolled based on the inclusion/exclusion criteria described below. All subjects were able to walk, sit down and stand up on their own. Screening procedures not already performed in the context of their care for cancer was done prior to the study. A total of 24 subjects (12 each group) completed the protocol. The inclusion criteria were as follows: (1) Radiographic evidence of cancer, (2) Age>40 years (both male and female), (3) Ability to sign informed consent.

Overview of the Study Design.

A randomized, controlled, double-blind, parallel-group design in 24 patients with recently diagnosed metastatic colorectal cancer was utilized. Subjects were initially interviewed, and the experimental procedures were explained in detail and signed, informed consents obtained. After acceptance into the study, subjects received all of their meals for 3 days prior to the experimental phase of the study to standardize food intake. The meals were prepared to be taken home to be eaten. The evening before the study the subjects refrained from any food or drink (except water) intake from 22:00 hr onwards. The experimental phase of the study started the following morning and lasted for approximately 10 hours. Twelve patients ingested the sip feed containing the specific nutritional combination (SNC) and the other 12 patients ingested a control supplement (CS). Each subject ingested 400 ml of the supplements in two doses. The intake of the second dose started twenty minutes after the first sip of the first dose. Each dose was consumed within 10 minutes. Subjects were randomly assigned with respect to the supplement to be ingested, stratified for gender.

Experimental Procedures.

On the morning of the study two 18-22 gauge catheters were placed by the study nurse into veins of the right and left forearms, and one used for blood sampling and the other for tracer infusion. After obtaining a blood sample for background amino acid enrichment and fasting blood glucose, a priming or "loading" (2 µmol/kg) infusion of U-13C6-phenylalanine was given. This was immediately followed by a continuous (0.07 µmol/kg/min) infusion of U-13C6-phenylalanine and maintained throughout the experiment. A muscle biopsy was performed at 2 hours after the start of isotope infusion and again at 5 hours. Blood was also taken from the sampling forearm catheter periodically for the determination of amino acid enrichments (plasma tracer/tracee ratio). Immediately following the second muscle biopsy, one dose of the supplement (200 ml) was given, followed by a second dose (200 ml) 20 minutes after the first sip of the first dose. Each dose was consumed within 10 minutes. The third muscle biopsy was taken 300 minutes after the first sip of the first dose of supplement. The subjects were lying in bed throughout the study unless they had to use the bathroom. Muscle biopsies were used to calculate muscle protein fractional synthetic rate (FSR). Plasma samples were analyzed for amino acid enrichments (plasma tracer/tracee ratio) glucose and amino acid concentrations.

Results.

Muscle protein synthesis was similar at base line for SNC and control group (each n=12 patients) (see FIG. 5). Ingestion of 400 ml of control sip resulted in a fractional synthesis rate similar to baseline synthesis rate, while supplementation with the specific nutritional combination according to the invention (SNC), resulted in an increase in fractional synthesis rate of 1.4 times the fractional synthesis rate at baseline.

Glucose concentrations were reduced in patients receiving the composition according to the invention (SNC) when compared to patients receiving the control supplement (FIG. 6). This is advantageous because low post prandial glucose levels can (on term) result in improved sensitivity of the muscle for an anabolic triggers (insulin).

Example 4

Glycemic Index Determination

Definition.

The glycemic index (GI) of a carbohydrate provides a measure of its ability to raise postprandial glucose concentrations. High GI foods give higher postprandial blood glucose levels than those with a low GI. The GI of a carbohydrate also predicts the insulin response to that food.

The GI of a carbohydrate is calculated by assessing a 25 g two-hour glycaemic response with that of a subsequent 25 g carbohydrate standard glucose:

GI equals 'Incremental area under blood glucose response curve for a test food containing 25 g of carbohydrate' divided by 'Corresponding area after equivalent carbohydrate portion of glucose'

Glycaemic Index Methodology.

Available carbohydrate is defined for GI testing purposes as: Total carbohydrate minus the indigestible carbohydrates (soluble and insoluble) that are from a physiological point dietary fibres (e.g. inulin, FOS, type 3 resistant starch).

The samples provided should be representative of the product as available to the consumer in the market place.

All foods submitted for testing are tested in vivo, that is, in 10 human subjects consuming amounts containing the equivalent of 25 g available carbohydrate. They are healthy subjects with no chronic diseases, diabetes or glucose impairment. Subjects have a BMI between 18.5-27 kg/m$^2$.

Reference food: The reference food is 25 g glucose powder dissolved in 250 mls water. Each person tests the reference food at least twice.

Test foods: The test foods are prepared according to manufacturer's instructions, representing the food as normally consumed. The test foods are consumed once only on separate occasions as a portion providing 25 g of available carbohydrate, defined as above.

Protocol Subjects: Subjects are tested in the morning after a 10-12 h overnight fast. Two fasting blood samples are taken (−5 & 0) 5 minutes apart after which subjects consume the test meal or reference food at an even rate over 15 minutes. Further blood samples are taken at 15, 30, 45, 60, 90 and 120 minutes after the beginning of the meal. The test meal and reference food should be consumed with a 250 mls drink of water. This remains constant for each of the tests in the series.

24 hrs prior to GI test: The day before each session, subjects refrain from drinking alcohol and avoid unusual levels of exercise and food intake. Subjects must have an evening meal based on a carbohydrate-rich food, such as rice, pasta, bread, potatoes and not too much fat. This meal should not include beans, pulses or legumes (to avoid a second meal effect the next morning). It is important that they eat dinner and not fast for more than 18 hours. Subjects are asked to be in a similar state each time they come in for a session. After they have eaten their evening meal, subjects fast for at least 10 hours overnight before the start of their test session the next morning. They can drink only water during the fasting period.

Blood sampling: Blood will be obtained by finger pricking.

Blood is collected without clotting inhibitors (heparin, EDTA).

Glucose assay: Whole capillary blood or is measured by an automatic glucose analyzer. In this case, Hemocue glucose analysers are used.

Data analysis: The incremental area under the blood glucose response curve (iAUC), ignoring area beneath the baseline, is calculated geometrically as follows:

For times t0, t1, . . . tn the blood glucose concentrations are G0, G1, . . . Gn, respectively:

$$iAUC = \sum_{n}^{x=1} Ax$$

wherein Ax=the AUC for the xth time interval (ie. between tx−1 and tx).

For the first time interval (ie. x=1): if G1>G0, A1=(G1−G0)×(t1−t0)/2 otherwise, A1=0

For the other time intervals (ie. x>1)

if Gx≥G0 and Gx−1≥G0, Ax={[(Gx−G0)/2]+(Gx−1−G0)/2}×(tx−tx−1)

if Gx>G0 and Gx−1<G0, Ax=[(Gx−G0)$^2$/(Gx−Gx−1)]×(tx−tx−1)/2 if Gx<G0 and Gx−1>G0, Ax=[(Gx−1−G0)$^2$/(Gx−1−Gx)]×(tx−tx−1)/2 if Gx≤G0 and Gx−1≤G0, Ax=0

GI calculation: In individual subjects, the GI value is the iAUC for each food expressed as a percentage of the mean iAUC of the two reference foods (glucose). The GI of the test food is the mean GI±SEM of the 10 subjects.

Up to two outliers (an outlier is an individual whose GI differs from the mean by more than two SD) may be excluded from the data set. SEM should be within 20% of the mean.

Clinical Trial Setting 1: Healthy Volunteers.

Ten healthy subjects having a BMI between 18.5-27 kg/m2, were tested after a 10-12 h fast. Each subject was tested in a cross over design, receiving 25 g of carbohydrates from a standard reference glucose drink (2 times), a standard sip (16 EN % protein, 50 EN % carbohydrates and 34 EN % fat) or the test drink according to the invention ("SNCGI value was calculated as the incremental area under the blood glucose response curve for each food (iAUC) as a percentage of the mean iAUC of the reference glucose drink.

Results.

The GI for the standard sip was 67±10 whereas the GI for the test drink was 40±4. Therefore the GI of Forticare was classified as low (<55) and the standard sip as medium (55-70).

Clinical Trial Setting 2: Cancer Patients:

As described in Example 3 Glucose concentrations were reduced in patients receiving the specific nutritional combination SNC when compared to patients receiving the control supplement (Example 3, FIG. 5).

What is claimed:

1. A combination of proteinaceous matter comprising
   (a) at least 18 en % of proteinaceous matter, wherein the proteinaceous matter includes at least 10% whey protein based on total proteinaceous matter;
   (b) at least 12 wt % of leucine, based on total proteinaceous matter;
   (c) an indigestible carbohydrate comprising one or more of galactooligosaccharides or fructooligosaccharides; and
   (d) a lipid fraction comprising fish oil, wherein the fish oil comprises at least 10 wt % based on total lipid content of an ω-3 polyunsaturated fatty acid being eicosapentaenoic acid, docosahexaenoic acid, eicosatetraenoic acid or docosapentaenoic acid, for use in the improvement of a muscle function in a mammal.

2. The combination of claim 1 wherein the muscle function is skeletal muscle function.

3. The combination of claim 2, wherein improving skeletal muscle function comprises improving muscle mass dependent loss of muscle function comprising a correction in maximal force, maximal contraction velocity or maximal relaxation velocity of skeletal muscle.

4. The combination of claim 2, wherein improving skeletal muscle function comprises improving muscle mass independent loss of muscle function comprising a correction in maximal force corrected for muscle mass, maximal contraction velocity corrected for muscle mass or maximal relaxation velocity corrected for muscle mass.

5. The combination of claim 1, wherein improving the muscle function is improving reduced muscle function due to, or resulting from aging, disease, disorder, drugs or trauma.

6. The combination of claim 5, wherein the disease or disorder is cancer, HIV-infection, COPD, renal failure, heart failure, or a disease state characterized by a high plasma or serum level of pro-inflammatory cytokines.

7. The combination according to claim 5, wherein improving the muscle function is improving reduced muscle function due to chemotherapy.

8. The combination of claim 1, wherein the combination is a liquid, comprising at least 7 g/100 ml of proteinaceous matter.

9. The combination of claim 1, wherein the proteinaceous matter further comprises at least one protein from a protein source of casein, caseinate, soy or wheat.

10. The combination of claim 1, wherein the proteinaceous matter comprises at least 15 wt %, of whey, based on the total proteinaceous matter.

11. The combination of claim 1 comprising 12 to 23 wt % of leucine, based on total proteinaceous matter.

12. The combination of claim 1 comprising 16 to 28 wt % of glutamine based on total proteinaceous matter.

13. The combination of claim 1 comprising at least 0.7 wt % of one or more of cystine, cysteine or cysteine equivalents, based on total proteinaceous matter.

14. The combination of claim 1 including carnitine or taurine.

15. The combination of claim 1 comprising at least 15 wt % of an ω-3 polyunsaturated fatty acid, based on total lipid content.

16. The combination of claim 1, wherein the indigestible carbohydrate is a galactomannan having a degree of polymerisation (DP) between 2 and 50, xylans having a DP of 2 to 60, oligomers having more than 30 wt % of galacturonic acid or glucuronic acid moieties having a molecular weight of 520 to 2200 Dalton, and any combination thereof.

17. The combination of claim 1, wherein the indigestible carbohydrate content amounts 1 to 15 wt %, based on total dry matter.

18. A composition comprising proteinaceous matter, a lipid, and a digestible carbohydrate, wherein
   a) the proteinaceous matter content provides 18 to 60 en % of the total composition, said proteinaceous matter comprising at least 10% whey protein based on total proteinaceous matter and at least 12 wt % of leucine, based on total proteinaceous matter;
   b) the lipid content provides 10 to 50 en % of the total composition, said lipid comprising fish oil, wherein the fish oil comprises at least 10 wt % based on total lipid content of an ω-3 polyunsaturated fatty acid being eicosapentaenoic acid, docosahexaenoic acid, eicosatetraenoic acid or docosapentaenoic acid;
   c) the digestible carbohydrate content provides 20 to 70 en % of the total composition.

19. The combination of claim 1 wherein the improvement in muscle function improves daily activity, physical performance, prognosis in terms of extended life-expectancy, compliance to an anti-cancer therapy or a quality of life.

20. The combination of claim 1, wherein the combination is a liquid, comprising at least 8 g/100 ml of proteinaceous matter.

21. The combination of claim 1, wherein the combination is a liquid, comprising at least 9 g/100 ml of proteinaceous matter.

22. The combination of claim 1, wherein the combination is a liquid, comprising at least 10 g/100 ml of proteinaceous matter.

23. The combination of claim 1, wherein the proteinaceous matter further comprises at least one protein from a protein source of casein.

24. The combination of claim 1, wherein the proteinaceous matter comprises at least 25 wt % of whey, based on the total proteinaceous matter.

25. The combination of claim 1 comprising a galactooligosaccharide and a fructooligosaccharide in a molar ratio of galactooligosaccharide to fructooligosaccharide in the range from 1:1 to 20:1.

26. Nutritional composition comprising a combination of
   (a) at least 18 en % of proteinaceous matter, said proteinaceous matter comprising whey;
   (b) at least 12 wt % of leucine, based on total proteinaceous matter; and
   (c) a lipid fraction comprising at least an ω-3 polyunsaturated fatty acid selected from the group of eicosapentaenoic acid, docosahexaenoic acid, eicosatetraenoic acid and docosapentaenoic acid,
      for use in the improvement of the muscle function in a mammal.

* * * * *